(12) United States Patent
Barr

(10) Patent No.: US 9,637,763 B2
(45) Date of Patent: May 2, 2017

(54) RECOMBINANT PRODUCTION SYSTEMS FOR AROMATIC MOLECULES

(75) Inventor: Philip J. Barr, Oakland, CA (US)

(73) Assignee: RHO Renewables, Inc., Oakland, CA (US)

( * ) Notice: Subject to any disclaimer, the term of this patent is extended or adjusted under 35 U.S.C. 154(b) by 67 days.

(21) Appl. No.: 14/128,540

(22) PCT Filed: Jun. 22, 2012

(86) PCT No.: PCT/US2012/043878
§ 371 (c)(1),
(2), (4) Date: Mar. 5, 2014

(87) PCT Pub. No.: WO2012/178110
PCT Pub. Date: Dec. 27, 2012

(65) Prior Publication Data
US 2014/0220648 A1    Aug. 7, 2014

Related U.S. Application Data

(60) Provisional application No. 61/583,325, filed on Jan. 5, 2012, provisional application No. 61/500,518, filed on Jun. 23, 2011.

(51) Int. Cl.
| | | |
|---|---|---|
| C12P 7/22 | (2006.01) | |
| C12P 7/00 | (2006.01) | |
| C12N 1/00 | (2006.01) | |
| C12N 15/00 | (2006.01) | |
| C12P 21/06 | (2006.01) | |
| C12P 19/34 | (2006.01) | |
| C07H 21/04 | (2006.01) | |
| C12N 9/88 | (2006.01) | |
| C12N 9/10 | (2006.01) | |
| C12N 9/12 | (2006.01) | |
| C12N 15/52 | (2006.01) | |
| C12P 17/04 | (2006.01) | |

(52) U.S. Cl.
CPC .............. *C12P 7/22* (2013.01); *C12N 9/1007* (2013.01); *C12N 9/1288* (2013.01); *C12N 9/88* (2013.01); *C12N 15/52* (2013.01); *C12P 7/00* (2013.01); *C12P 17/04* (2013.01)

(58) Field of Classification Search
CPC ........ C12N 9/88; C12N 9/1007; C12N 15/52; C12N 9/1288; C12P 7/22; C12P 17/04; C12P 7/00
USPC ........... 435/156, 132, 254.11, 254.2, 254.23, 435/254.3, 320.1, 69.1, 91.1; 536/23.1, 536/23.2
See application file for complete search history.

(56) References Cited

U.S. PATENT DOCUMENTS

| | | |
|---|---|---|
| 4,407,661 A | 10/1983 | Dolhyj et al. |
| 4,683,195 A | 7/1987 | Mullis et al. |
| 5,130,242 A | 7/1992 | Barclay |
| 5,231,178 A | 7/1993 | Holtz et al. |
| 5,324,639 A | 6/1994 | Brierley et al. |
| 5,397,591 A | 3/1995 | Kyle et al. |
| 5,407,957 A | 4/1995 | Kyle et al. |
| 5,420,034 A | 5/1995 | Kridl et al. |
| 5,492,938 A | 2/1996 | Kyle et al. |
| 5,530,194 A | 6/1996 | Knauf et al. |
| 5,711,983 A | 1/1998 | Kyle et al. |
| 6,033,883 A | 3/2000 | Barr et al. |
| 6,258,566 B1 | 7/2001 | Barr et al. |
| 6,607,900 B2 | 8/2003 | Bailey et al. |
| 7,078,233 B2 | 7/2006 | Barr et al. |
| 7,256,023 B2 | 8/2007 | Metz et al. |
| 7,323,320 B2 | 1/2008 | Oleinikov |
| 2006/0160138 A1 | 7/2006 | Church et al. |
| 2007/0269870 A1 | 11/2007 | Church et al. |
| 2008/0064610 A1 | 3/2008 | Lipovsek et al. |
| 2008/0287320 A1 | 11/2008 | Baynes et al. |
| 2009/0087840 A1 | 4/2009 | Baynes et al. |

FOREIGN PATENT DOCUMENTS

| | | |
|---|---|---|
| EP | 0116718 | 5/1990 |
| EP | 0120516 | 10/1991 |
| WO | WO 95/08548 | 3/1995 |
| WO | WO 98/27203 | 6/1998 |
| WO | WO 98/55625 | 10/1998 |
| WO | WO 02/052024 | 7/2002 |
| WO | WO 2006/086457 | 8/2006 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Vainstein et al., Rose fragrance: Genomic approaches and Metabolic Engineering. Proc. 21st ISHS on Classical/molecular Breeding, Ed: G. Forkman et al. Acta Hort, 2003, vol. 612: 105-113.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*

(Continued)

*Primary Examiner* — Ganapathirama Raghu
(74) *Attorney, Agent, or Firm* — Benjamin C. Pelletier; Arnold & Porter Kaye Scholer LLP

(57) ABSTRACT

The invention relates to the production of aromatic molecules in prokaryotic and eukaryotic hosts such as *E. coli*, yeasts, filamentous fungi, algae, microalgae, other plant cells.

14 Claims, 4 Drawing Sheets

(56) References Cited

OTHER PUBLICATIONS

Gaucher et al., Isolation of orsellinic acid synthase. Biochem. Biophys. Res. Commun., 1968, vol. 32 (4): 664-671.*
Fieschko et al. "Controlled expression and purification of human immune interferon from high-cell-density fermentations of Saccharomyces cerevisiae", Biotechnology and Bioengineering 29:1113-1121, 1987.
Artigot et al. "Molecular cloning and functional characterization of two CYP619 cytochrome P450s involved in biosynthesis of patulin in aspergillus clavatus", Microbiology 155(5):1738-1747, 2009.
Beachy et al. "Accumulation and assembly of soybean β-conglycinin in seeds of transformed petunia plants", EMBO Journal 4(12):3407-3053, 1985.
Beck et al. "The multifunctional 6-methylsalicylic acid synthase gene of penicillium patulum. Its gene structure relative to that of other polyketide synthases", Eur J. Biochem. 192(2):487-498, 1990.
Bevan et al. "Structure and transcription of the nopaline synthase gene region of T-DNA", Nucleic Acids Res. 11(2):369-85, 1983.
Binet et al. "Analysis of a sunflower polyubiquitin promoter by transient expression", Plant Science 79:87-94, 1991.
Brignon et al. "Constitutive and cell-division-inducible protein-DNA interactions in two maize histone gene promoters", Plant Journal 4(3):445-457, 1993.
Christensen et al. "Maize polyubiquitin genes: structure, thermal perturbation of expression and transcript splicing, and promoter activity following transfer to protoplasts by electroporation", Plant Mol Biol 18(4):675-689, 1992.
Ding et al. "Insights into bacterial 6-methylsalicylic acid synthase and its engineering to orsellinic acid synthase for spirotetronate generation", Chemistry & Biology 17(5):495-503, 2010.
Ellis et al. "Maize Adh-1 promoter sequences control anaerobic regulation: addition of upstream promoter elements from constitutive genes is necessary for expression in tobacco", EMBO Journal 6(1):11-16, 1987.
Elliott et al. "Yeast-derived recombinant human insulin-like growth factor I: production, purification, and structural characterization", Journal Protein Chemistry 9(1):95-104, 1990.
Fieschko et al. "Controlled expression and purification of human immune interferon from high-cell-density fermentations of Saccharomyces cerevisiae", Biotechnol. Bioeng. 29:1113-1121, 1987.
Kealey et al. "Production of a polyketide natural product in nonpolyketide-producing prokaryotic and eukaryotic hosts", Pro. Natl. Acad. Sci USA 95(2):505-509, 1998.
Khaden et al. "Monocyclic phenolic acids; hydroxy-and polyhydroxybenzoic acids: occurrence and recent bioactivity studies", Molecules 15(11):7985-8005, 2010.
Langridge et al. "Dual promoter of agrobacterium tumefaciens mannopine synthase genes is regulated by plant growth hormones", Proc Natl. Acad. Sci. USA 86(6):3219-3223, 1989.
Lawton et al. "Expression of a soybean β-conclycinin gene under the control of the cauliflower mosaic virus 35S and 19S promoters in transformed petunia", Plant Mol. Biol. 9(4):315-324, 1987.
Light, RJ. "6-methylsalicylic acid decarboxylase from penicillium patulum", Biochim. Biophys. Acta 191(2):430-438, 1969.
Ma et al. "Complete reconstitution of a highly reducing iterative polyketide synthase", Science 326(5952):589-592, 2009.
McElroy et al. "Isolation of an efficient actin promoter for use in rice transformation", Plant Cell 2(2):163-171, 1990.
Mosbach et al. "Studies on lichen enzymes. Purification and properties of orsellinate decarboxylase obtained from lasallia pustulata", European J. Biochemistry 22(4):485-488, 1971.
Mutka et al. "Metabolic pathway engineering for complex polyketide biosynthesis in Saccharomyces cerevisiae", FEMS Yeast Research 6(1):40-47, 2006.
Nunberg et al. "Developmental and hormonal regulation of sunflower helianthinin genes: proximal promoter sequences confer regionalized seed expression", Plant Cell 6(4):473-486, 1984.
Odell et al. "Identification of DNA sequences required for activity of the cauliflower mosaic virus 35S promoter", Nature 313(6005):810-812, 1985.
Packter, NM. "Studies on the biosynthesis of quinones in fungi. Incorporation of 6-methylsalicylic acid into fumigatin and related compounds in aspergillus fumigatus I.M.I. 89353", Biochemical Journal 97(2):321-332, 1965.
Pettersson et al. "An orsellinic acid decarboxylase isolated from gliocladium roseum", Acta Chemica Scandinavica 19:2013-2021,1965.
Plant et al. "Regulation of an Arabidopsis oleosin gene promoter in transgenic Brassica napus", Plant Mol Biol 25(2):193-205, 1994.
Roje et al. "Metabolic engineering in yeast demonstrates that S-adenosylmethionine controls flux through the methylenetetrahydrofolate reductase reaction in vivo", J. Biol Chem 277(6):4056-4061, 2002.
Scalliet et al. "Biosynthesis of the major scent components 3,5-dimethoxytoluene and 1,3,5-trimethoxybenzene by novel rose 0-methyltransferases", FEBS Letters 523(1-3);113-118, 2002.
Sengupta-Gopalan et al. "Developmentally regulated expression of the bean beta-phaseolin gene in tobacco seed", Proc Natl. Acad. Sci. USA 82(10):3320-3324, 1985.
Slater et al. "The decarboxylation of 6 methyl salicylic-acid by valsa-friessi", Canadian Journal Microbiology, NRC Research Press, CA 19(9):1169-1171, 1973.
Thompson et al. "Primary structures of the precursor and mature forms of stearoyl-acyl carrier protein desaturase from safflower embryos and requirement of ferredoxin for enzyme activity", Proc Natl. Acad. Sci. USA 88(6):2578-2582, 1991.
Truksa et al. "Molecular analysis of flax 2S storage protein conlinin and seed specific activity of its promoter", Plant Physiology and Biochemistry 41:141-147, 2003.
Tsai et al. Development of a methyltrophic yeast dicistronic expression vector by the Saccharomyces cerevisiae internal ribosomal entry sites.(IRES), 1998 http://gra103.aca.ntu.edu.tw/gdoc/98/D92B47403a.pdf).
Wattanachaisaereekul et al. "Production of the polyketide 6-MSA in yeast engineered for increased malonyl-CoA supply", Metabolic Engineering, Academic Press 10(5):246-254, 2008.
Wattanachaisaereekul et al. "Optimization of heterologous production of the polyketide 6-MSA in Saccharomyces cerevisiae" Biotech Bioeng 97:893-900, 2007.
Xie et al. "Microbial synthesis of triacetic acid lactone", Biotechnology and Bioengineering 93(4):727-736, 2006.

* cited by examiner

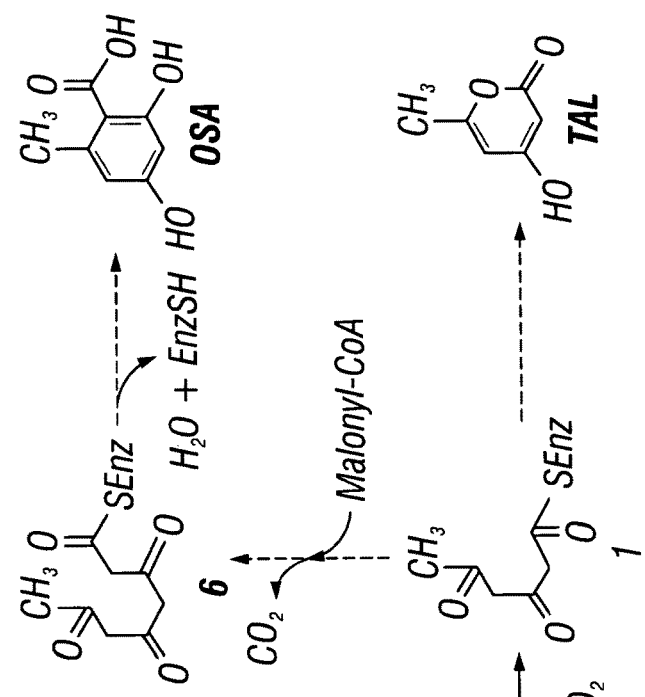
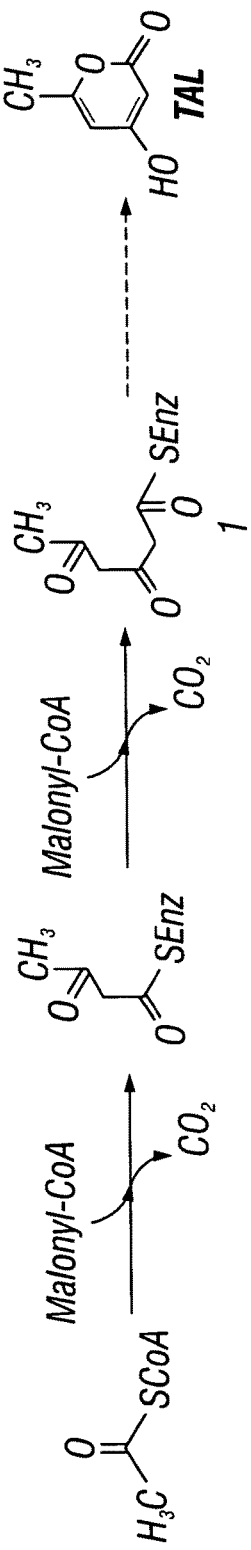
FIG. 2A
FIG. 2B

*Figure 1. 6-Methylsalicylic Acid Synthase and Orsellinic Acid Synthase, and Biosyntheses of 6-MSA, Triacetic Acid Lactone, and Orsellinic Acid*

RECOMBINANT PRODUCTION SYSTEMS FOR AROMATIC MOLECULES

CROSS-REFERENCE TO RELATED APPLICATIONS

This application is a U.S. national stage continuation application claiming the benefit of, and priority under 35 U.S.C. §371 from international application PCT/US2012/043878, filed Jun. 22, 2012, which claims the benefit of, and priority under 35 U.S.C. §119 to, U.S. Provisional Patent Application Ser. No. 61/583,325, filed Jan. 5, 2012, and U.S. Provisional Patent Application Ser. No. 61/500,518, filed Jun. 23, 2011 all of which applications are hereby incorporated by reference in their entireties.

FIELD OF THE INVENTION

The invention relates to the production of aromatic molecules in prokaryotic and eukaryotic hosts such as *E. coli*, yeasts, filamentous fungi, algae, microalgae, other plant cells.

BACKGROUND OF THE INVENTION

There currently exists an unfulfilled need for the production of many specialty chemicals, and liquid fuels, from renewable resources. Despite a great negative impact on the environment, the earth's oceans and atmosphere, the great majority of chemical compounds and motor vehicle fuels are still derived from fossil fuels such as crude oil, coal tar, shale oil and so on. Of particular note, simple phenolic compounds such as the cresols, are largely extracted from coal tar in a process that has such a negative impact on the environment that U.S. factories specializing in cresol production have been closed in recent years. This, however, is not a global solution, as the problem may simply be transferred to another geographical location. Synthetic biology offers potential solutions to the manufacture of certain specialty chemicals such as these.

Polyketides generally are synthesized by condensation of two-carbon units in a manner analogous to fatty acid synthesis. In general, the synthesis involves a starter unit and extender units; these "two-carbon" units are derived from, for example, acylthioesters, typically acetyl, propionyl, malonyl or methylmalonyl coenzyme-A thioesters. There are four classes of polyketide synthases (PKSs) that differ in the "manner" in which the catalytic sites are used (Watanabe and Ebizuka, 2004). The type I modular PKSs are single proteins with multiple "modules" that contain catalytic sites that are used only once in linear "assembly-line" style. The type I iterative PKSs are single proteins with sites that are used repeatedly to reach the final polyketide product. The present invention can employ coding sequences from each of the classes, but in preferred embodiments, the PKSs employed will be derived primarily from this class of PKS, e.g. the aromatic 6-methylsalicylic acid synthases, or the orsellinic acid synthases, or modified versions of these enzymes. Genes encoding polypeptide components of type I PKSs have been used for the microbiological production of polyketides in heterologous microorganisms such as yeast and *E. coli*. See for example U.S. Pat. Nos. 6,033,883, 6,258,566, and 7,078,233.

The type II PKSs contain multiple proteins, each with a single monofunctional active site. The active sites may be used only once, or repeatedly. Lastly, type III PKSs are single proteins with multiple modules, in which the active sites are used repeatedly.

The PKSs operate in an analogous way to the fatty acid synthases (FASs). Fatty acids are generally composed of hydrophobic components and can also be used as an energy source, such as in biofuels. Many eukaryotes synthesize fatty acids using common or similar metabolic pathways. In seeds, fatty acids, as part of triglycerides, are stored as a source of energy for further germination. The FAS pathway is located in the plastids. Acetyl-ACP (acyl carrier protein) is formed by a condensing enzyme, β-ketoacyl-ACP synthase (KAS) III. Elongation of the acetyl-ACP to longer chain fatty acids involves the cyclical action of the condensation of a 2-carbon unit from malonyl-ACP to form a longer β-ketoacyl-ACP (β-ketoacyl-ACP synthase), reduction of the keto function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I (KAS I), is primarily responsible for elongation up to palmitoyl-ACP (C16:0), whereas β-ketoacyl-ACP synthase II (KAS II) is predominantly responsible for the final elongation to stearoyl ACP (C18:0).

Similarly, iterative aromatic PKSs utilize the condensation of a 2-carbon unit from malonyl-ACP to form products such as 6-methylsalicylic acid (6-MSA), also known as 2-hydroxy-6-methylbenzoic acid (HMBA), and orsellinic acid (OSA) via the biosynthetic pathways shown in FIGS. 1 and 2. The flexibility of these pathways is underscored by the fact that a bacterial 6-MSAS can be engineered to synthesize OSA simply by "knocking out" the catalytic activity of the ketoreductase (KR) domain (Ding et al., Chemistry & Biology 17, 495-503, 2010).

The present invention provides systems for production of molecules and precursor molecules with multiple uses in the microbicidal, pharmaceutical and renewable liquid fuel areas. In some embodiments, addition of the machinery for pantetheinylation of the acyl carrier proteins (i.e., using a holo ACP synthase, also known as a PPTase) permits production of said molecules in a wide spectrum of hosts that may not necessarily produce such molecules naturally.

The aromatic molecules thus obtained directly or indirectly from the microbial hosts, such as cresols, orcinols, hydroxymethylbenzoic acids and their cognate ethers, esters and lactones, yield homogeneous or heterogeneous preparations of compounds that are, or can be further treated to yield compounds suitably used as microbicidals, pharmaceuticals, vitamins, flavoring agents or renewable energy sources, such as a fuel, a fuel additive, such as an oxygenate, a fuel adjunct, i.e. a high octane gasoline blending agent and so on.

SUMMARY OF THE INVENTION

Figure 1:
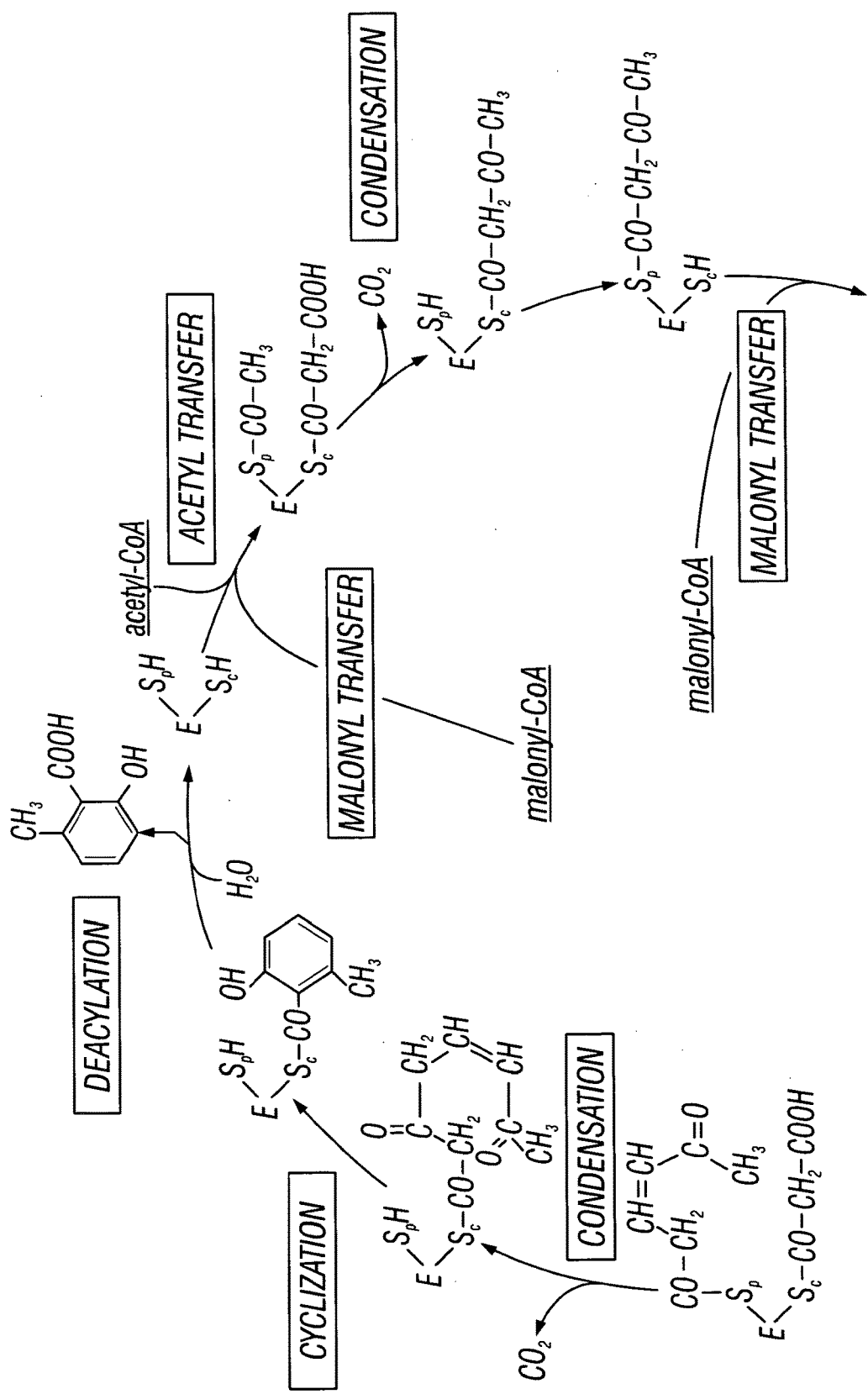
FIG. 1 depicts the biosynthesis pathway of 6-MSA (Beck et al., Eur J Biochem 192:487-498 (1990)).
Figure 1:
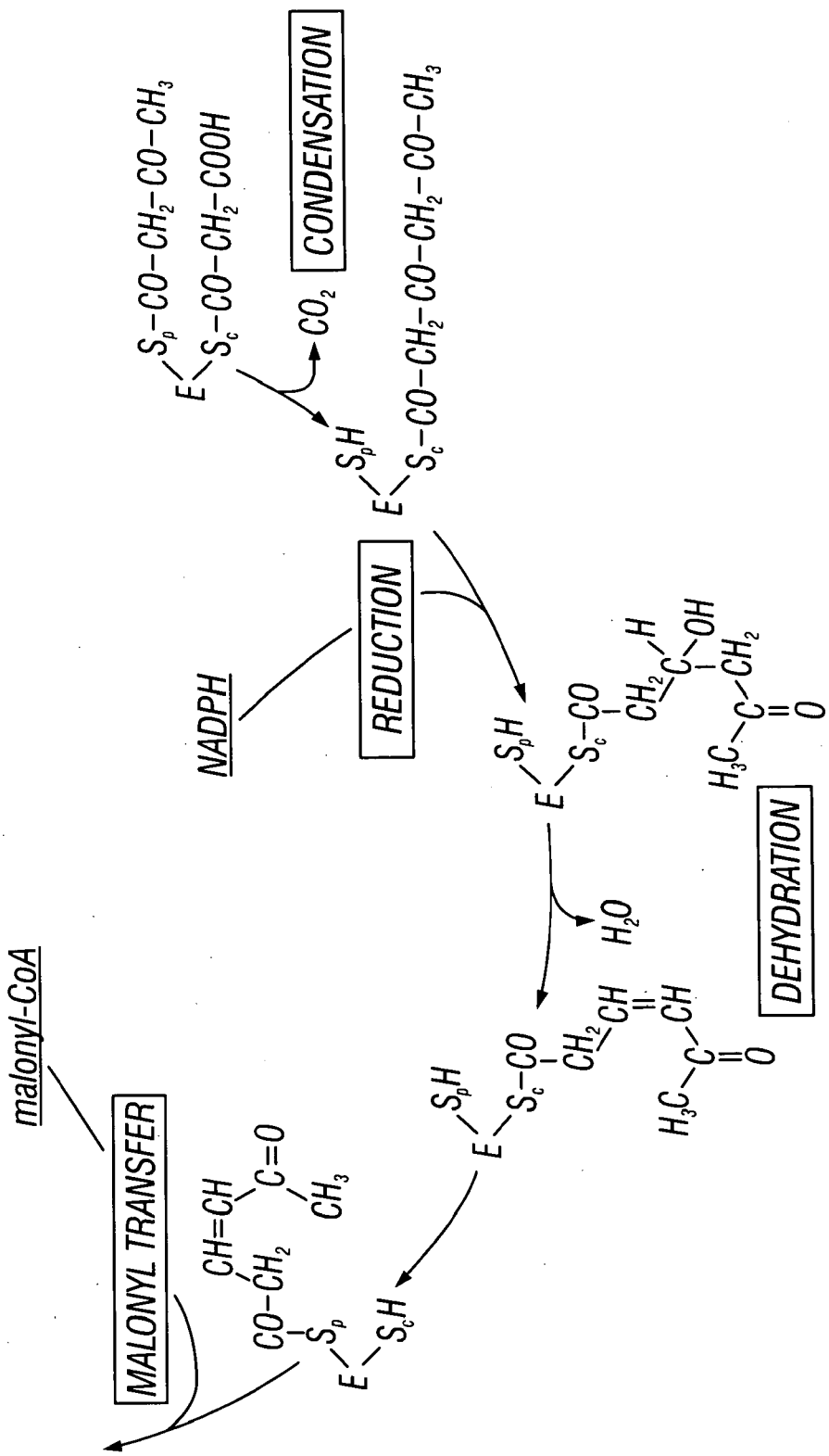

The present invention relates to the production of aromatic molecules in prokaryotic and eukaryotic hosts such as *E. coli*, yeasts, filamentous fungi, algae, microalgae, other plant cells and so on. In one aspect, the molecules are obtained using functional aromatic polyketide synthases (PKSs) and the resulting variety of molecules are transformed in vivo to make specialty chemicals for microbicidal or pharmaceutical use. In addition, the present invention contemplates the production of precursors of compounds for microbicidal or pharmaceutical use. In one aspect, the precursors are treated further to yield high octane aromatic or cyclohexane and cyclohexanol-like molecules that can be precursors for additional specialty chemicals and polymers. The treated precursors may be compatible with petroleum-based and jet fuels and can, therefore, be used as a renewable energy source.

The invention relates to recombinant materials for the production and derivatization of polyketides in a variety of hosts and the resultant polyketides and their derivatives. Single or multiple vectors can be used to construct the hosts for producing the compounds, as known in the art. Single vectors enable minimal treatment of the host cells, multiple vectors facilitate the ability for further in vivo transformations and permit more flexibility in designing various novel synthetic pathways.

In one embodiment, the present invention provides a modified recombinant host cell for producing a phenolic compound, comprising i) a first expression system that comprises at least one nucleotide sequence that encodes an aromatic polyketide synthase (PKS) for 6-methylsalicylic acid (6-MSAS), capable of being expressed. In another embodiment, the host cell further comprises ii) a second expression system that comprises at least one nucleotide sequence that encodes a holo acyl carrier protein (ACP) synthase, wherein the ACP synthase pantetheinylates said PKS. In an additional embodiment, the host cell further comprises iii) a third expression system that comprises at least one nucleotide sequence that encodes a decarboxylase. In one other embodiment, the product isolated from said cell is a phenolic compound. In another embodiment, the aromatic PKS is the synthase for 6-methylsalicylic acid from a prokaryote. In one other embodiment, the expression system for 6-MSAS from a prokaryote comprises a functional decarboxylase present on the same vector, or on a separate vector. In one other embodiment, the aromatic PKS is encoded by the ChlB1 gene from *S. antibioticus* in wild-type form. In one additional embodiment, the phenolic compound that is capable of being produced by the cell and capable of being isolated from the cell is meta-cresol.

In one embodiment, the aromatic PKS comprises an inactivated ketoreductase (KR) domain. In another embodiment, the aromatic PKS is the synthase for 6-methylsalicylic acid from a fungus. In an additional embodiment, the aromatic PKS is the orsellinic acid synthase (OSAS) encoded by the AviM gene from *Streptomyces viridochromogenes*. In another embodiment, the phenolic compound that is capable of being produced by the cell and capable of being isolated from the cell is orcinol.

In another embodiment, the nucleotide sequence encoding the decarboxylase is selected from the group consisting of the 6-MSA decarboxylase gene from *P. patulum*, the PatG gene from *Aspergillus clavatus*, the OSA decarboxylase gene from *Gliocladium roseum*, the 2,3-dihydroxybenzoic acid decarboxylase genes from *Aspergillus* species, and the 5-carboxyvanillate decarboxylase gene from *Sphingomonas paucimobilis* SYK-6.

In another embodiment, the expression system for said PKS and the expression system for said holo ACP synthase are present on the same vector. In other embodiments, the expression system for said PKS and said expression system for said holo ACP synthase are present on separate vectors.

In one other embodiment, the PKS and said holo ACP synthase are expressed from a dicistronic messenger RNA.

In one other embodiment, the modified cell comprises an expression system for a functional decarboxylase is present on the same vector as either expression system for said minimal PKS or said expression system for said holo ACP synthase, or on a separate vector. In another embodiment, the expression system for said minimal PKS and said expression system for said holo ACP synthase and said expression system for a functional decarboxylase are present on the same vector. In one embodiment, one, two or all three of said expression systems are integrated into the host cell chromosome or expressed from yeast artificial chromosomes (YACs). In other embodiments, at least two of the expressed PKS, holo ACP synthase and decarboxylase are derived from a multicistronic messenger RNA. In another embodiment, the host organism is selected from the group consisting of *Pichia pastoris*, and an *Aspergillus* species. In one embodiment, the host organism is *Aspergillus niger*. In another embodiment, the *Aspergillus niger* does not contain a heterologous expression system for a holo ACP synthase.

In another aspect, the present invention provides a method of producing a phenolic compound. In one embodiment, the method comprises the step of a) providing a modified recombinant host cell comprising i) a first expression system that comprises at least one nucleotide sequence encoding an aromatic polyketide synthase (PKS) for 6-methylsalicylic acid (6-MSAS), capable of being expressed; ii) a second expression system that comprises at least one nucleotide sequence encoding a holo acyl carrier protein (ACP) synthase, wherein the ACP synthase pantetheinylates said PKS; and iii) a third expression system that comprises at least one nucleotide sequence that encodes a decarboxylase. In another embodiment, the method further comprises b) producing a phenolic compound intermediate in the recombinant host cell. In one other embodiment, the method further comprises c) synthesizing a phenolic compound from the phenolic compound intermediate, wherein recombinant decarboxylase catalyzes decarboxylation of the phenolic compound intermediate to form the phenolic compound. In one embodiment, the phenolic compound intermediate is 6-MSA. In another embodiment, the phenolic compound is meta-cresol.

In one embodiment, the aromatic PKS comprises an inactivated ketoreductase (KR) domain. In another embodiment, the aromatic PKS is an orsellinic acid synthase (OSAS) encoded by the AviM gene from *Streptomyces viridochromogenes*. In some embodiments, the phenolic compound intermediate is orsellinic acid (OSA). In other embodiments, the phenolic compound is orcinol.

In another aspect, the present invention provides a method of producing a phenolic compound. In one embodiment, the method comprises a) providing a modified recombinant host cell comprising i) a first expression system that comprises at least one nucleotide sequence encoding an aromatic polyketide synthase (PKS) for 6-methyl salicylic acid (6-MSAS), capable of being expressed; and ii) a second expression system that comprises at least one nucleotide sequence encoding a holo acyl carrier protein (ACP) synthase, wherein the ACP synthase pantetheinylates said PKS. In one embodiment, the method further comprises b) isolating a phenolic compound intermediate produced in the recombinant host cell. In one embodiment, the method further comprises c) decarboxylating the phenolic compound intermediate of step b) to form the phenolic compound by heating with a metal catalyst (or other type of catalyst) followed by distillation. In an additional embodiment, the phenolic compound intermediate is 6-MSA. In other embodiments, the phenolic compound is meta-cresol. In one embodiment, the metal catalyst is in a powdered form. In another embodiment, the metal catalyst is a zinc catalyst.

In one other aspect, the present invention provides a modified recombinant host cell for producing an alkylated phenolic compound. In one embodiment, the cell comprises i) a first expression system that comprises at least one nucleotide sequence that encodes an aromatic polyketide synthase (PKS) for 6-methylsalicylic acid (6-MSAS), capable of being expressed, and ii) a second expression system that comprises at least one nucleotide sequence that encodes a holo acyl carrier protein (ACP) synthase, wherein the ACP synthase pantetheinylates said PKS, iii) a third expression system that comprises at least one nucleotide sequence that encodes a decarboxylase, and (iv) a fourth expression system that comprises at least one nucleotide sequence that encodes an O-methyltransferase (OMT). In one embodiment, the product capable of being produced by the cell and capable of being isolated from said cell is an alkylated phenolic compound. In one embodiment, the alkylated phenolic compound is 3-methylanisole.

In one embodiment, the aromatic PKS comprises an inactivated ketoreductase (KR) domain. In another embodiment, the aromatic PKS is the orsellinic acid synthase (OSAS) encoded by the AviM gene from *Streptomyces viridochromogenes*. In one additional embodiment, the alkylated phenolic compound is 3,5-dimethoxytoluene.

In an additional embodiment, the OMT is encoded by a *Rosa chinensis* gene selected from the group consisting of OOMT1, OOMT2, OOMT3, OOMT4, COMT1.

In another aspect, the present invention provides a method of producing a alkylated phenolic compound. In one embodiment, the method comprises a) providing a modified recombinant host cell comprising i) a first expression system that comprises at least one nucleotide sequence encoding an aromatic polyketide synthase (PKS) for 6-methyl salicylic acid (6-MSAS), capable of being expressed; ii) a second expression system that comprises at least one nucleotide sequence encoding a holo acyl carrier protein (ACP) synthase, wherein the ACP synthase pantetheinylates said PKS; and iii) a third expression system that comprises at least one nucleotide sequence that encodes a decarboxylase. In another embodiment, the method further comprises b) isolating a phenolic compound intermediate produced in the recombinant host cell. In one embodiment, the method further comprises c) alkylating the phenolic compound intermediate of step b) to form the alkylated phenolic compound by treating with a alkylating agent. In another embodiment, the alkylating agent is methanol.

In one embodiment, the alkylated phenolic compound intermediate is m-cresol. In another embodiment, the alkylated phenolic compound is 3-methylanisole.

In another embodiment, the aromatic PKS comprises an inactivated ketoreductase (KR) domain. In one embodiment, the aromatic PKS is the orsellinic acid synthase (OSAS) encoded by the AviM gene from *Streptomyces viridochromogenes*. In one embodiment, the alkylated phenolic compound intermediate is orcinol. In one other embodiment, the alkylated phenolic compound is 3,5-dimethoxytoluene.

In another aspect, the present invention provides a method of producing a phthalic anhydride compound, the method comprising a) providing a modified recombinant host cell comprising i) a first expression system that comprises at least one nucleotide sequence encoding an aromatic polyketide synthase (PKS) for 6-methyl salicylic acid (6-MSAS), capable of being expressed; ii) a second expression system that comprises at least one nucleotide sequence encoding a holo acyl carrier protein (ACP) synthase, wherein the ACP synthase pantetheinylates said PKS. In another embodiment, the method further comprises b) isolating a phthalic anhydride intermediate compound produced in the recombinant host cell. In one other embodiment, the method further comprises c) oxidizing the phthalic anhydride intermediate compound of step b) to form the phthalic anhydride compound by treating with an oxidizing agent. In one embodiment, the phthalic anhydride intermediate compound is 6-MSA. In another embodiment, the phthalic anhydride is 3-hydroxyphthalic anhydride.

DESCRIPTION OF THE INVENTION

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted. Before the present methods, kits and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

"PKS" refers to a polyketide synthase (e.g., a 6-MSAS or OSAS).

"ACP" refers to an acyl carrier protein.

"ACPS" refers to an acyl carrier protein synthase (e.g., a holo ACP synthase).

"DC" refers to a decarboxylase.

"PKS*" refers to a modified polyketide synthase or PKS variant (e.g., PKS with an inactive ketoreductase domain).

"6-MSAS" refers to 6-methylsalicylic acid synthase.

"OSAS" refers to orsellinic acid synthase.

"OOMT" refers to orcinol O-methyltransferase.

"6-MSA" refers to 6-methylsalicylic acid.

"OSA" refers to orsellinic acid.

"HMBA" refers to 2-hydroxy-6-methylbenzoic acid.

All patents, patent applications, and literature references cited in the present specification are hereby incorporated by reference in their entirety.

The present invention provides methods and materials for producing organic compounds of interest in a rapid, inexpensive and efficient manner. As such, the present invention meets a number of commercial and industrial needs. The term "organic molecule" refers, for example, to any molecule that is made up predominantly of carbon and hydrogen, such as, for example, aromatic compounds. Organic compounds of interest include, without limitation, phenolics or phenolic compounds, such as 6-MSA/HMBA, OSA, meta-cresol, orcinol; 3-methylanisole; 3,5-dimethoxytoluene; and phthalates such as phthalic anhydride (e.g., 3-hydroxyphthalic anhydride).

In particular, the microbial production of the compounds of interest (e.g., meta-cresol, orcinol, methylanisoles) and their derivatives from renewable resources is contemplated by the present invention. The aromatics are obtained using functional aromatic polyketide synthases (PKSs) and the resulting variety of molecules are transformed in vivo to make specialty chemicals for microbicidal or pharmaceutical use, or to make precursors of compounds for microbicidal or pharmaceutical use, or are treated further to yield high octane aromatic or cyclohexane and cyclohexanol-like molecules that can be precursors for additional specialty chemicals and polymers, or are compatible with petroleum-based and jet fuels and can, therefore, be used as a renewable energy source.

In one aspect, the present invention relates to the synthesis of phenolics, phenolic compound, and phenolic compound intermediates. As used herein, a phenolic or phenolic compound refers to an organic compound which includes a phenyl group (—C$_6$H$_5$) bonded to a hydroxyl group (—OH).

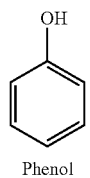

Phenol

In a preferred embodiment, the phenolic or phenolic compound is m-cresol (also known as 3-methylphenol) or orcinol (also known as 5-methylbenzene-1,3-diol).

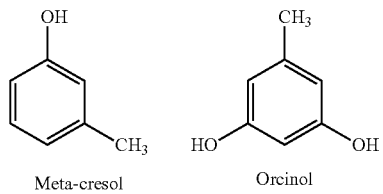

Meta-cresol        Orcinol

Figure 2B:
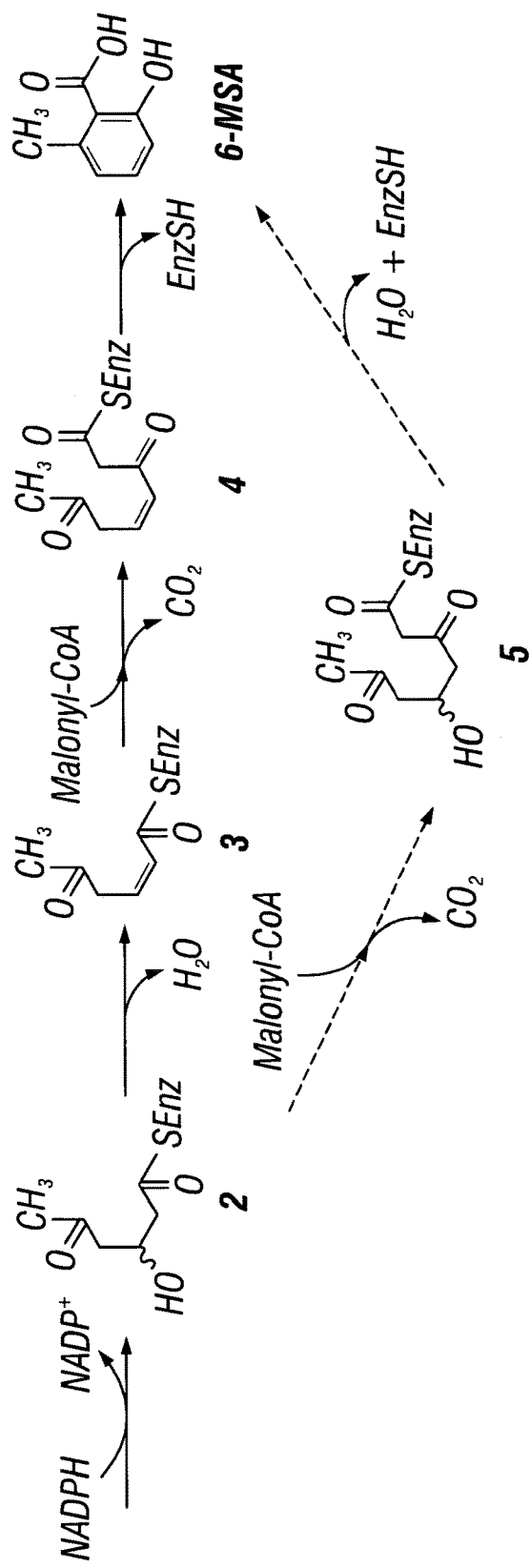
FIG. 2 depicts the biosynthesis pathway of 6-MSA and OSA (Ding et al., Chemistry and Biology 17:495-503 (2010)).

The present invention also concerns the synthesis of phenolic compound intermediates. In one embodiment, the phenolic compound intermediate is a compound produced in one of the steps in a metabolic pathway described herein (e.g., FIG. 1 and FIG. 2). The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. In one embodiment, each step of the metabolic pathway occurs in a modified recombinant cell described herein. In another embodiment, at least one step of the metabolic pathway occurs in a modified recombinant cell described herein, and at least one step of the metabolic pathway occurs outside the modified recombinant cell. The compounds produced at each step of the metabolic pathway may be called "intermediates" or "intermediate compounds" or "compound intermediates".

In one embodiment, the metabolic pathway comprises an enzymatic reaction catalyzed by one or more of the following: 6-MSAS; OSAS; holo ACP synthase; decarboxylase, O-methyltransferase; and any combination thereof. Such metabolic pathways are capable of producing the compounds of interest, as well as intermediate compounds, which are described herein.

In another embodiment, the metabolic pathway comprises an enzymatic reaction catalyzed by i) 6-MSAS or OSAS; and ii) holo ACP synthase. In one embodiment, the metabolic pathway comprises pantetheinylation of the 6-MSAS by the holo ACP synthase. In one other embodiment, the compound produced from the metabolic pathway is 6-MSA or OSA. In one embodiment, the 6-MSA or OSA is a phenolic compound intermediate. In another embodiment, the 6-MSA is a phthalic anhydride intermediate compound.

In one embodiment, the phenolic compound intermediate is selected from the group consisting of 6-methylsalicylic acid (6-MSA) (also know as 2-hydroxy-6-methylbenzoic acid (HMBA)) and orsellinic acid (OSA). In another embodiment, the recombinant cells and methods described herein provide for the synthesis of a phenolic compound of interest from the phenolic compound intermediate. In one other embodiment, m-cresol is synthesized from the 6-MSA intermediate or orcinol is synthesized from the OSA intermediate.

In another embodiment, the 6-MSA is a phthalic anhydride intermediate compound. In one other embodiment, the recombinant cells and methods described herein provide for the synthesis of a phthalic anhydride compound from the phenolic compound intermediate.

In another embodiment, the metabolic pathway comprises an enzymatic reaction catalyzed by i) PKS (e.g., 6-MSAS, modified 6-MSAS or OSAS); ii) holo ACP synthase; and iii) decarboxylase. In one other embodiment, the compound produced from the metabolic pathway is m-cresol or orcinol.

In another embodiment, the metabolic pathway comprises an enzymatic reaction catalyzed by i) PKS (e.g., 6-MSAS, modified 6-MSAS or OSAS); ii) holo ACP synthase; and iii) decarboxylase. In one other embodiment, the compound produced from the metabolic pathway is a methylated phenolic compound intermediate. In another embodiment, the methylated phenolic intermediate compound is m-cresol or orcinol. In one embodiment, the m-cresol is an intermediate for 3-methylanisole and orcinol is an intermediate for 3,5-dimethoxytoluene.

In another embodiment, the metabolic pathway comprises an enzymatic reaction catalyzed by i) PKS (e.g., 6-MSAS, modified 6-MSAS or OSAS); ii) holo ACP synthase; iii) decarboxylase; and iv) 0-methyltransferase. In one other embodiment, the compound produced from the metabolic pathway is a methylated phenolic compound. In one embodiment, the reaction is catalyzed by 6-MSAS, holo ACP synthase, a decarboxylase, and OOMT to yield 3-methylanisole. In one other embodiment, the reaction is catalyzed by a modified 6-MSAS (or OSAS), holo ACP synthase, a decarboxylase, and OOMT to yield 3,5-dimethoxytoluene.

In another aspect, the present invention relates to the production of organic compounds of interest in a microorganism and provides methods for the production of such compounds from a carbohydrate source in a microorganism.

The method incorporates microorganisms capable of producing one of the following organic compounds of interest, particularly, 6-methylsalicylic acid (6-MSA) (also known as 2-hydroxy-6-methylbenzoic acid (HMBA)), m-cresol, orcinol, 3-methylanisole; 3,5-dimethoxytoluene, toluene, and phthalates. The present invention provides engineered metabolic routes, isolated nucleic acids or engineered nucleic acids, polypeptides or engineered polypeptides, host cells or genetically engineered host cells, methods and materials to produce organic compounds of interest.

In another aspect, the present invention relates to engineered polypeptides and polynucleotides encoding the enzymes having an activity or an improved activity on a natural or an unnatural substrate or having broad substrate specificity. The term "polypeptide" and the terms "protein" and "peptide" which are used interchangeably herein, refers to a polymer of amino acids, including, for example, gene products, naturally-occurring proteins, homologs, orthologs, paralogs, fragments, and other equivalents, variants and analogs of the forgoing. The term "polypeptide having enzymatic activity" refers to any polypeptide that catalyzes a chemical reaction of other substances without itself being destroyed or altered upon completion of the reaction. Typically, a polypeptide having enzymatic activity catalyzes the formation of one or more products from one or more substrates. In some embodiments, existing enzymes are modified for use in organic biosynthesis. In some preferred embodiments, the enzymes involved in the production of the organic compounds of interest include but are not limited to 6-methylsalicylic acid (6-MSAS); orsellinic acid synthase (OSAS); holo acyl carrier protein (ACP) synthase; decarboxylase, and O-methyltransferase (OMT). In one embodiment, the enzyme is 6-MSAS comprising an inactivated ketoreductase (KR) domain. In another embodiment, the 6-MSAS comprising an inactivated KR domain facilitates production of orsellinic acid in the modified recombinant cells and by the methods described herein.

The invention in various aspects employs various components of an aromatic PKS system, or modified forms thereof or portions of more than one of these, coupled with additional modification enzymes to arrive at the desired product.

Iterative or "aromatic" PKS systems that are utilized in the present invention are characterized by the iterative use of the catalytic sites of the enzymes produced. Thus, in these aromatic PKS systems, only one enzyme with a specific type of activity is produced to catalyze the relevant activity for the system throughout the synthesis of the polyketide.

In some embodiments, the reaction mechanism of the enzyme may be altered to catalyze new reactions, to change, expand or improve substrate specificity. One should appreciate that if the enzyme structure (e.g. crystal structure) is known, enzymes properties may be modified by rational redesign (see US patent application US20060160138, US20080064610 and US20080287320 which are incorporated by reference in their entirety). Modification or improvement in enzyme properties may arise from introduction of modifications into a polypeptide chain that may, in effect, perturbs the structure-function of the enzyme and/or interaction with another molecule (e.g., substrate versus unnatural substrate). It is well known in the art that some regions of the polypeptide may be critical to enzyme activity. For example, small perturbation in composition of amino acids involved in catalysis and/or in substrate binding domains will have significant effects on enzyme function. Some amino acid residues may be at important positions for maintaining the secondary or tertiary structure of the enzyme, and thus also produce noticeable changes in enzyme properties when modified. In some embodiments, the potential pathway components are variants of any of the foregoing. Such variants may be produced by random mutagenesis or may be produced by rational design for production of an enzymatic activity having, for example, an altered substrate specificity, increased enzymatic activity, greater stability, etc. Thus, in some embodiments, the number of modifications to a reference parent enzyme that produces an enzyme having the desired property may comprise one or more amino acids, 2 or more amino acids, 5 or more amino acids, 10 or more amino acids, or 20 or more amino acids, up to 10% of the total number of amino acids, up to 20% of the total number of amino acids, up to 30% of the total number of amino acids, up to 40% of the total number of amino acids making up the reference enzyme or up to 50% of the total number of amino acids making up the reference enzyme. In one embodiment, the reference or parent enzyme is 6-MSAS which is modified to remove a ketoreductase (KR) domain. In another embodiment, the modified 6-MSAS lacking the KR domain is capable of producing orsellinic acid in a cell or by a method described herein.

Those skilled in the art will understand that engineered pathways exemplified herein are described in relation to, but are not limited to, species specific genes and encompass homologs or orthologs of nucleic acid or amino acid sequences. Homologs and orthologs sequences possess a relatively high degree of sequence identity/similarity when aligned using methods known in the art.

Aspects of the invention relates to new microorganisms or "genetically modified" microorganisms or host cells that have been engineered to possess new metabolic capabilities or new metabolic pathways. As used herein the term "genetically modified" microorganisms refers to microorganisms having at least one genetic alteration not normally found in the wild type strain of the references species. In some embodiments, genetically engineered microorganisms are engineered to express or overexpress at least one particular enzyme at critical points in a metabolic pathway, and/or block the synthesis of other enzymes, to overcome or circumvent metabolic bottlenecks.

Aspects of the invention provide methods for designing and making engineered metabolic pathways. In some aspects of the invention, alternative pathways for making a product of interest from one or more available and sustainable substrates may be made in one or more host cell or microorganisms of interest. One should appreciate that the engineered pathway for making the compounds of interest may involve multiple enzymes and therefore the flux through the pathway may not be optimum for the production of the product of interest. Consequently, in some aspects of the invention flux is optimally balanced by modulating the activity level of the pathway enzymes relative to one another. Examples of such modulation are provided throughout the application.

In one aspect, the present invention provides genetically modified host cells or microorganism and methods of using the same to produce organic compounds of interest. A host cell as used herein refers to an in vivo or in vitro eukaryotic cell, a prokaryotic cell or a cell from a multicellular organism (e.g. cell line) cultured as a unicellular entity. A host cell may be prokaryotic (e.g., bacterial such as *E. coli* or *B. subtilis*) or eukaryotic (e.g., a yeast, mammal or insect cell).

For example, host cells may be bacterial cells (e.g., *E. coli, Bacillus subtilis, Mycobacterium* spp., *M. tuberculosis*, or other suitable bacterial cells), Archaea (for example, *Methanococcus Jannaschii* or *Methanococcus Maripaludis* or other suitable archaic cells), yeast cells (for example, *Saccharomyces* species such as *S. cerevisiae, S. pombe, Picchia* species, *Candida* species such as *C. albicans*, or other suitable yeast species).

It should be noted that in some recombinant hosts, it might also be necessary to activate the polyketides produced through post-synthetic modifications when polyketides having antibiotic activity are desired. If this is the case for a particular host, the host will be modified, for example, by transformation, to contain those enzymes necessary for effecting these modifications. Among such enzymes, for example, are glycosylation enzymes.

Thus, to produce, for example, the polyketides of the invention, suitable hosts are modified to contain vectors, typically plasmids, which contain expression systems for the production of proteins with one or more of the activities associated with PKS. By placing various activities on different expression vectors, a high degree of variation can be achieved. A variety of hosts can be used, such as naturally occurring cells, genetically engineered cells, such as, transgenic cells, synthetic cells and so on; any suitable host cell for which selection markers can be devised to assure the incorporation of multiple vectors can readily be used. Preferred host cells include yeast, *E. coli*, and other bacteria, such as acetogens and *Streptomyces* species, fungi such as *Neurospora* and *Aspergillus* species, actinomycetes, *Clostridium* species, such as, *C. acetobutylicum*, which produces n-butanol, *Methanosaeta thermophila, Micrococcus luteus*, which produces long chain alkenes, *Vibrio furnissii*, such as the M1 strain, which produces n-alkanes, and plant cells, although there is no theoretical reason why mammalian or insect cells or other suitable recombinant hosts could not be used. Preferred among yeast strains are *Saccharomyces cerevisiae* and *Pichia pastoris*. Preferred plant cells are algal cells, such as single cell algal forms, diatoms and so on. However, other types and strains may be useful as having the inherent PKS enzymes of interest, see, for example, WO 98/55625. Hence, U.S. Pat. No. 7,256,023 teaches a polyunsaturated fatty acid polyketide synthase for making, for example, DHA and EPA, omega-3 oils which are alleged to have health benefits. Preferred host cells for carrying that synthase are, for example, *Schizochytrium*, which is a *Thraustochytrid* marine microorganism that accumulates large quantities of triacylglycerols rich in DHA and docosapentaenoic acid.

Plant cells, and in some embodiments, single cell plant cells, can be used in the practice of the instant invention. For example, the following species can be used as host for the vector systems of interest: *Neochloris oleoabundans*, a microalga belonging in the class Chlorophyceae; *Scenedesmus dimorphus*, a unicellular alga in the class Chlorophyceae, preferably maintained under constant agitation; *Euglena gracilis; Phaeodactylum tricornutum*, a diatom; *Pleurochrysis carterae*, a unicellular coccolithophorid alga that has the ability to calcify subcellularly, a member of the class Haptophyta (Prymnesiophyceae); *Prymnesium parvum; Tetraselmis chui*, a marine unicellular alga; *Tetraselmis suecica; Isochrysis galbana*, a microalga; *Nannochloropsis salina*, also called *Nannochloris oculata*, is in the same group as *Nannochloris atomus* Butcher, *Nannochloris maculata* Butcher, *Nannochloropsis gaditana* Lubian, and *Nannochloropsis oculata* (Droop); *Botryococcus braunii*, a green alga; *Dunaliella tertiolecta*, a fast growing strain that has a high $CO_2$ sequestration rate as well, and so on.

The choice of hosts, of course, dictates the choice of the control sequences associated with the expression system as well as the selectable markers. Suitable promoter systems, for example, for use in *E. coli* include the tryptophan (trp) promoter, the lactose (lac) promoter, the T7 promoter and the λ-derived $P_L$ promoter and N-gene ribosome-binding site. For yeast, suitable control sequences include promoters for the synthesis of glycolytic enzymes, such as glyceraldehyde-3-phosphate dehydrogenase (GAPDH), 3-phosphoglycerate kinase (PGK). Other promoters include those for alcohol dehydrogenases (ADH-1 and ADH-2), isocytochrome-C, acid phosphatase, degradative enzymes associated with nitrogen metabolism and enzymes responsible for maltose and galactose utilization. It is also known that terminator sequences are desirable at the 3' end of the coding sequences.

Fermentation methods may be adapted to a particular yeast strain due to differences in their carbon utilization pathway or mode of expression control. For example, a *Saccharomyces* yeast fermentation may require a single glucose feed, complex nitrogen source (e.g., casein hydrolyzates), and multiple vitamin supplementation. This is in contrast to the methylotrophic yeast *Pichia pastoris* which may require glycerol, methanol, and trace mineral feeds, but only simple ammonium (nitrogen) salts, for optimal growth and expression. See, e.g., Elliott et al. J. Protein Chem. (1990) 9:95 104, U.S. Pat. No. 5,324,639 and Fieschko et al. Biotechnol. Bioeng. (1987) 29:1113 1121.

There are a number of methanol responsive genes in methylotrophic yeast, the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *P. pastoris* AOX2, the promoter for the dihydroxyacetone synthase gene from *P. pastoris* (DAS), the promoter for the P40 gene from *P. pastoris*, the promoter for the catalase gene from *P. pastoris*, and the like. Suitable media for use with *Pichia* are described in U.S. Pat. Nos. 5,231,178 and 5,324,639.

Illustrative examples of suitable host cells include any archae, bacterial, or eukaryotic cell. Examples of archae cells include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae species include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium*.

Examples of bacterial cells include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Illustrative examples of bacterial species include but are not limited to: *Bacillus subtilis, Bacillus amyloliquefacines*,

*Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

The anaerobic bacteria may be one strain of bacteria or a mixed culture containing two or more of acetogenic bacteria, including, without limitation, *Acetobacterium kivui, A. woodii, Butyribacterium methylotrophicum, Clostridium aceticum, C. acetobutylicum, C. formoaceticum, C. kluyveri, C. thermoaceticum, C. thermocellum, C. thermohydrosulfuricum, C. thermosaccharolyticum, Eubacterium limosum, Lactobacillus casei, Peptostreptococcus productus*, and *C. ljungdahlii*, and mixtures thereof.

In some embodiments, anaerobic bacterial organisms are metabolically engineered. As used herein, an anaerobic organism is any organism that does not require oxygen for growth (i.e. anaerobic conditions) Advantageously, the bacterial cell can be an *E. coli, C. glutanicum, B. flavum* or *B. lactofermentum* cell; these strains are currently being employed industrially to make amino compounds using bacterial fermentation processes. For example, *C. glutanicum* has been used extensively for amino acid production (e.g. L-glutamate, L-Lysine, see Eggleging L et al., 2005, Handbook for *Corynebacterium glutanicum*. Boca Raton, USA: CRC Press).

In general, if a bacterial host cell is used, a non-pathogenic strain is preferred. Illustrative examples of species with non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of eukaryotic cells include but are not limited to fungal cells. Examples of fungal cells include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic species include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccaromyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of species with non-pathogenic strains include but are not limited to: *Fusarium graminearum, Fusarium venenatum, Pichia pastoris, Saccaromyces boulardi*, and *Saccaromyces cerevisiae*.

In some embodiments, organisms include those selected from the group consisting of golden algae (such as microorganisms of the kingdom Stramenopiles), green algae, diatoms, dinoflagellates (such as microorganisms of the order Dinophyceae including members of the genus *Crypthecodinium* such as, for example, *Crypthecodinium cohnii*), yeast, and fungi of the genera *Mucor* and *Mortierella*, including but not limited to *Mortierella alpina* and *Mortierella sect. schmuckeri*. Members of the microbial group Stramenopiles include microalgae and algae-like microorganisms, including the following groups of microorganisms: Hamatores, Proteromonads, Opalines, Develpayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinaales, Pedinellales, Dictyochales), Chrysomeridales, Sarcinochrysidales, Hydrurales, Hibberdiales, and Chromulinales. The Thraustochytrids include the genera *Schizochytrium* (species include *aggregatum, limnaceum, mangrovei, minutum, octosporum*), *Thraustochytrium* (species include *arudimentale, aureum, benthicola, globosum, kinnei, motivum, multirudimentale, pachydermum, proliferum, roseum, striatum*), *Ulkenia* (species include *amoeboidea, kerguelensis, minuta, profunda, radiate, sailens, sarkariana, schizochytrops, visurgensis, yorkensis*), *Aplanochytrium* (species include *haliotidis, kerguelensis, profunda, stocchinoi*), *Japonochytrium* (species include *marinum*), *Althornia* (species include *crouchii*), and *Elina* (species include *marisalba, sinorifica*). The Labrinthulids include the genera *Labyrinthula* (species include *algeriensis, coenocystis, chattonii, macrocystis, macrocystis atlantica, macrocystis macro cystis, marina, minuta, roscoffensis, valkanovii, vitellina, vitellina pacifica, vitellina vitellina, zopfi*), *Labyrinthomyxa* (species include *marina*), *Labyrinthuloides* (species include *haliotidis, yorkensis*), *Diplophrys* (species include *archeri*), *Pyrrhosorus\** (species include *marinus*), *Sorodiplophrys\** (species include *stercorea*), *Chlamydomyxa\** (species include *labyrinthuloides, montana*).

Suitable organisms can be obtained from a number of available sources, including by collection from the natural environment. For example, the American Type Culture Collection currently lists many publicly available strains of microorganisms identified above. As used herein, any organism, or any specific type of organism, includes wild strains, mutants, or recombinant types. Growth conditions in which to culture or grow these organisms are known in the art, and appropriate growth conditions for at least some of these organisms are disclosed in, for example, U.S. Pat. No. 5,130,242, U.S. Pat. No. 5,407,957, U.S. Pat. No. 5,397,591, U.S. Pat. No. 5,492,938, U.S. Pat. No. 5,711,983 and U.S. Pat. No. 6,607,900, all of which are incorporated herein by reference in their entirety. Preferably, the effective medium also promotes rapid microbial growth. The microorganisms can be cultured in conventional fermentation modes, which include, but are not limited to, batch, fed-batch, and continuous.

In a further embodiment of the invention, transgenic plants are selected from the group comprising cereals, soybean, rapeseed (including oil seed rape, especially canola and winter oil seed rape), cotton sugarcane and potato, especially corn, soy, rapeseed (including oil seed rape, especially canola and winter oil seed rape), cotton, wheat and rice.

In another embodiment of the invention the transgenic plant is a gymnosperm plant, especially a spruce, pine or fir.

In one preferred embodiment, the host plant is selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants and in particular plants mentioned herein above as host plants such as the families and genera mentioned above for example preferred the species *Anacardium occidentale, Calendula officinalis, Carthamus tinctorius, Cichorium intybus, Cynara scolymus, Helianthus annus, Tagetes lucida, Tagetes erecta, Tagetes tenuifolia; Daucus carota; Corylus avellana, Corylus colurna, Borago officinalis; Brassica napus, Brassica rapa* ssp., *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis, Brassica oleracea, Arabidopsis thaliana, Anana comosus, Ananas ananas, Bromelia comosa, Carica papaya, Cannabis sative, Ipomoea batatus, Ipomoea pandurata, Convolvulus batatas, Convolvulus tiliaceus, Ipomoea fastigiata, Ipomoea tiliacea, Ipomoea triloba, Convolvulus panduratus, Beta vulgaris, Beta vulgaris* var. *altissima, Beta vulgaris* var. *vulgaris, Beta maritima, Beta vulgaris* var. *perennis, Beta vulgaris* var. *conditiva, Beta vulgaris* var. *esculenta, Cucurbita maxima, Cucurbita mixta, Cucurbita pepo, Cucurbita moschata, Olea europaea, Manihot utilissima, Janipha manihot., Jatropha manihot., Manihot aipil, Manihot dulcis, Manihot manihot, Manihot melanobasis, Manihot esculenta, Ricinus communis, Pisum sativum, Pisum arvense, Pisum humile, Medicago sativa, Medicago falcata, Medicago varia, Glycine max Dolichos soja, Glycine gracilis, Glycine hispida, Phaseolus max, Soja hispida, Soja max, Cocos nucifera, Pelargonium grossularioides, Oleum cocoas, Laurus nobilis, Persea americana, Arachis hypogaea, Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense, Linum trigynum, Punica granatum, Gossypium hirsutum, Gossypium arboreum, Gossypium barbadense, Gossypium herbaceum, Gossypium thurberi, Musa nana, Musa acuminata, Musa paradisiaca, Musa* spp., *Elaeis guineensis, Papaver orientale, Papaver rhoeas, Papaver dubium, Sesamum indicum, Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata, Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum, Avena sativa, Avena fatua, Avena byzantina, Avena fatua* var. *sativa, Avena hybrida, Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum, Zea mays, Triticum aestivum, Triticum durum, Triticum turgidum, Triticum hybernum, Triticum macha, Triticum sativum* or *Triticum vulgare, Cofea* spp., *Coffea arabica, Coffea canephora, Coffea liberica, Capsicum annuum, Capsicum annuum* var. *glabriusculum, Capsicum frutescens, Capsicum annuum, Nicotiana tabacum, Solanum tuberosum, Solanum melongena, Lycopersicon esculentum, Lycopersicon lycopersicum, Lycopersicon pyriforme, Solanum integrifolium, Solanum lycopersicum Theobroma cacao* or *Camellia sinensis.*

Anacardiaceae such as the genera *Pistacia, Mangifera, Anacardium* e.g. the species *Pistacia vera* [pistachios, Pistazie], *Mangifer indica* [Mango] or *Anacardium occidentale* [Cashew]; Asteraceae such as the genera *Calendula, Carthamus, Centaurea, Cichorium, Cynara, Helianthus, Lactuca, Locusta, Tagetes, Valeriana* e.g. the species *Calendula officinalis* [Marigold], *Carthamus tinctorius* [safflower], *Centaurea cyanus* [cornflower], *Cichorium intybus* [blue daisy], *Cynara scolymus* [Artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [lettuce], *Tagetes lucida, Tagetes erecta* or *Tagetes tenuifolia* [Marigold]; Apiaceae such as the genera *Daucus* e.g. the species *Daucus carota* [carrot]; Betulaceae such as the genera *Corylus* e.g. the species *Corylus avellana* or *Corylus colurna* [hazelnut]; Boraginaceae such as the genera *Borago* e.g. the species *Borago officinalis* [borage]; Brassicaceae such as the genera *Brassica, Melanosinapis, Sinapis, Arabadopsis* e.g. the species *Brassica napus, Brassica rapa* ssp. [canola, oilseed rape, turnip rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*; Bromeliaceae such as the genera *Anana, Bromelia* e.g. the species *Anana comosus, Ananas ananas* or *Bromelia comosa* [pineapple]; Caricaceae such as the genera *Carica* e.g. the species *Carica papaya* [papaya]; Cannabaceae such as the genera *Cannabis* e.g. the species *Cannabis sative* [hemp], Convolvulaceae such as the genera *Ipomea, Convolvulus* e.g. the species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, Man of the Earth, wild potato], Chenopodiaceae such as the genera *Beta*, i.e. the species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugar beet]; Cucurbitaceae such as the genera *Cucubita* e.g. the species *Cucurbita maxima, Cucurbita mixta, Cucurbita* pepo or *Cucurbita moschata* [pumpkin, squash]; Elaeagnaceae such as the genera *Elaeagnus* e.g. the species *Olea europaea* [olive]; Ericaceae such as the genera *Kalmia* e.g. the species *Kalmia latifolia, Kalmia angustifolia, Kalmia microphylla, Kalmia polifolia, Kalmia occidentalis, Cistus chamaerhodendros* or *Kalmia lucida* [American laurel, broad-leafed laurel, calico bush, spoon wood, sheep laurel, alpine laurel, bog laurel, western bog-laurel, swamp-laurel]; Euphorbiaceae such as the genera *Manihot, Janipha, Jatropha, Ricinus* e.g. the species

*Manihot utilissima, Janipha manihot, Jatropha manihot, Manihot aipil, Manihot dulcis, Manihot manihot, Manihot melanobasis, Manihot esculenta* [manihot, arrowroot, tapioca, cassaya] or *Ricinus communis* [castor bean, Castor Oil Bush, Castor Oil Plant, Palma Christi, Wonder Tree]; Fabaceae such as the genera *Pisum, Albizia, Cathormion, Feuillea, Inga, Pithecolobium, Acacia, Mimosa, Medicajo, Glycine, Dolichos, Phaseolus, Soja* e.g. the species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [bastard logwood, silk tree, East Indian Walnut], *Medicago sativa, Medicago falcata, Medicago varia* [alfalfa] *Glycine max Dolichos soja, Glycine gracilis, Glycine hispida, Phaseolus max, Soja hispida* or *Soja max* [soybean]; Geraniaceae such as the genera *Pelargonium, Cocos, Oleum* e.g. the species *Cocos nucifera, Pelargonium grossularioides* or *Oleum cocois* [coconut]; Gramineae such as the genera *Saccharum* e.g. the species *Saccharum officinarum*; Juglandaceae such as the genera *Juglans, Wallia* e.g. the species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut, black walnut, common walnut, persian walnut, white walnut, butternut, black walnut]; Lauraceae such as the genera *Persea, Laurus* e.g. the species laurel *Laurus nobilis* [bay, laurel, bay laurel, sweet bay], *Persea americana Persea americana, Persea gratissima* or *Persea persea* [avocado]; Leguminosae such as the genera *Arachis* e.g. the species *Arachis hypogaea* [peanut]; Linaceae such as the genera *Linum, Adenolinum* e.g. the species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [flax, linseed]; Lythrarieae such as the genera *Punica* e.g. the species *Punica granatum* [pomegranate]; Malvaceae such as the genera *Gossypium* e.g. the species *Gossypium hirsutum, Gossypium arboreum, Gossypium barbadense, Gossypium herbaceum* or *Gossypium thurberi* [cotton]; Musaceae such as the genera *Musa* e.g. the species *Musa nana, Musa acuminata, Musa paradisiaca, Musa* spp. [banana]; Onagraceae such as the genera *Camissonia, Oenothera* e.g. the species *Oenothera biennis* or *Camissonia brevipes* [primrose, evening primrose]; Palmae such as the genera *Elacis* e.g. the species *Elaeis guineensis* [oil palm]; Papaveraceae such as the genera *Papaver* e.g. the species *Papaver orientale, Papaver rhoeas, Papaver dubium* [poppy, oriental poppy, corn poppy, field poppy, shirley poppies, field poppy, long-headed poppy, long-pod poppy]; Pedaliaceae such as the genera *Sesamum* e.g. the species *Sesamum indicum* [sesame]; Piperaceae such as the genera *Piper, Artanthe, Peperomia, Steffensia* e.g. the species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata.* [Cayenne pepper, wild pepper]; Poaceae such as the genera *Hordeum, Secale, Avena, Sorghum, Andropogon, Holcus, Panicum, Oryza, Zea, Triticum* e.g. the species *Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum* [barley, pearl barley, foxtail barley, wall barley, meadow barley], *Secale cereale* [rye], *Avena sativa, Avena fatua, Avena byzantina, Avena fatua* var. *sativa, Avena hybrida* [oat], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum* [Sorghum, millet], *Oryza sativa, Oryza latifolia* [rice], *Zea mays* [corn, maize] *Triticum aestivum, Triticum durum, Triticum turgidum, Triticum hybernum, Triticum macha, Triticum sativum* or *Triticum vulgare* [wheat, bread wheat, common wheat], Proteaceae such as the genera *Macadamia* e.g. the species *Macadamia intergrifolia* [macadamia]; Rubiaceae such as the genera *Coffea* e.g. the species *Cofea* spp., *Coffea arabica, Coffea canephora* or *Coffea liberica* [coffee]; Scrophulariaceae such as the genera *Verbascum* e.g. the species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein, white moth mullein, nettle-leaved mullein, dense-flowered mullein, silver mullein, long-leaved mullein, white mullein, dark mullein, greek mullein, orange mullein, purple mullein, hoary mullein, great mullein]; Solanaceae such as the genera *Capsicum, Nicotiana, Solanum, Lycopersicon* e.g. the species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [egg-plant] (*Lycopersicon esculentum, Lycopersicon lycopersicum., Lycopersicon pyriforme, Solanum integrifolium* or *Solanum lycopersicum* [tomato]; Sterculiaceae such as the genera *Theobroma* e.g. the species *Theobroma cacao* [cacao]; Theaceae such as the genera *Camellia* e.g. the species *Camellia sinensis*) [tea].

Eukaryotic or prokaryotic host cells can be, or have been, genetically modified (also referred as "recombinant host cell", "metabolic engineered cells" or "genetically engineered cells") and are used as recipients for a nucleic acid, for example, an expression vector that comprises a nucleotide sequence encoding one or more biosynthetic or engineered pathway gene products. Eukaryotic and prokaryotic host cells also denote the progeny of the original cell which has been genetically engineered by the nucleic acid. In some embodiments, a host cell may be selected for its metabolic properties. For example, if a selection or screen is related to a particular metabolic pathway, it may be helpful to use a host cell that has a related pathway. Such a host cell may have certain physiological adaptations that allow it to process or import or export one or more intermediates or products of the pathway. However, in other embodiments, a host cell that expresses no enzymes associated with a particular pathway of interest may be selected in order to be able to identify all of the components required for that pathway using appropriate sets of genetic elements and not relying on the host cell to provide one or more missing steps.

The metabolically engineered cell of the invention is made by transforming a host cell with at least one nucleotide sequence encoding enzymes involved in the engineered metabolic pathways. As used herein the term "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In a preferred embodiment, the nucleotide sequence is codon-optimized to reflect the typical codon usage of the host cell without altering the polypeptide encoded by the nucleotide sequence. In certain embodiments, the term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a mean to control the level of expression of a polypeptide (e.g. either increase or decrease the level of expression). Accordingly, aspects of the invention include nucleic sequences encoding the enzymes involved in the engineered metabolic pathways. In some embodiments, a metabolically engineered cell may express one or more polypeptide having an enzymatic activity necessary to perform the steps described below. In one embodiment, the nucleotide sequence is codon-optimized for expression in yeast.

For example a particular cell may comprises one, two, three, four, five or more than five nucleic acid sequences, each one encoding the polypeptide(s) necessary to produce a phenolic compound, or phenolic compound intermediate described herein. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequences, DNA libraries, de novo synthesis, excision of genomic segment. The sequences obtained from such sources may then be modified using standard molecular biology and/or recombinant DNA technology to produce nucleic sequences having desired modifications. Exemplary methods for modification of nucleic acid sequences include, for example, site directed mutagenesis, PCR mutagenesis, deletion, insertion, substitution, swapping portions of the sequence using restriction enzymes, optionally in combination with ligation, homologous recombination, site specific recombination or various combination thereof. In other embodiments, the nucleic acid sequences may be a synthetic nucleic acid sequence. Synthetic polynucleotide sequences may be produce using a variety of methods described in U.S. Pat. No. 7,323,320, in copending application having Ser. No. 11/804,996, and in U.S. Patent Publication Nos. 2006/0160138 and 2007/0269870, which are incorporated herein by reference in their entirety.

Methods of transformation for bacteria, plant, and animal cells are well known in the art. Common bacterial transformation methods include electroporation and chemical modification.

In some embodiments, a genetically modified host cell is genetically modified such that it produces, when cultured in vitro in a suitable medium, the product of interest or an intermediate at a level of at least about 0.1 g/L, at least about 0.5 g/L, at least about 0.75 g/L, at least 1 g/L, at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 7 g/L, at least about 8 g/L, at least about 9 g/L, or at least 10 g/L.

One should appreciate that the level of the product of interest or its metabolic intermediates produced by a genetically modified host cell can be controlled in various ways. In some embodiments, the level of expression is controlled by the number of copy of the nucleic acid sequences encoding one or more enzymes involved in the engineered pathway (e.g. high copy expression vector versus medium or low copy expression vectors). Preferably, the nucleic acid sequences are introduced into the cell using a vector. Low copy expression vectors generally provide fewer than 20 vectors copies per cell (e.g. from 1 to about 5, from 5 to about 10, from 10 to about 15, from 15 to about 20 copies expression vector per cell. Suitable low copy expression vectors for prokaryotic cells (e.g. *E. Coli*) include, but are not limited to pAYC184, pBeloBac11, pBR332, pBAD33, pBBR1MCS and its derivatives, pSC101, SuperCos (cosmid) and pWE15 (cosmid). Medium copy number expression vectors generally provide from about 20 to about 50 expression vectors copies per cell or from about 20 to 80 expression vectors copies per cell). Suitable medium copy expression vectors for prokaryotic cells (e.g. *E. Coli*) include, but are not limited to pTrc99A, pBAD24 and vectors containing a ColE1 origin of replication and its derivatives. High copy number expression vectors generally provide from about 80 to about 200 or more expression vector copies per cell. Suitable high copy expression vectors for prokaryotic cells (e.g. *E. Coli*) include, but are not limited to, pUC, PCV1, pBluescript, pGEM and pTZ vectors.

In another aspect, the present invention provides expression cassettes comprising a nucleic acid or a subsequence thereof encoding a polypeptide involved in the engineered pathway. In some embodiments, the expression cassette can comprise the nucleic acid that is operably linked to a transcriptional element (e.g. promoter) and to a terminator. As used herein, the term "cassette" refers to a nucleotide sequence capable of expressing a particular gene if said gene is inserted so as to be operably linked to one or more regulatory sequences present in the nucleotide sequence. Thus, for example, the expression cassette may comprise a desired heterologous gene to be expressed in the host cell. In some embodiments, one or more expression cassettes may be introduced into a vector by known recombinant techniques. A promoter is a sequence of nucleotides that initiates and controls the transcription of a desired nucleic acid sequence by an RNA polymerase enzyme. In some embodiments, promoters may be inducible. In other embodiments, promoters may be constitutive. Non limiting examples of suitable promoters for the use in prokaryotic host cells include a bacteriophage T7 RNA polymerase promoter, a trp promoter, a lac operon promoter and the like. Non limiting example of suitable strong promoter for the use in prokaryotic cells include lacUV5 promoter, T5, T7, Trc, Tac and the like. Non limiting examples of suitable promoters for use in eukaryotic cells include a CMV immediate early promoter, a SV40 early or late promoter, a HSV thymidine kinase promoter and the like. Termination control regions may also be derived from various genes native to the preferred hosts.

Also in the present invention, in a further aspect, a promoter region associated with a coding region in filamentous fungus such as *A. niger, A. nidulans* or a related fungal species, such as *N. crassa* is identified and isolated, appropriately joined in a functional relationship with a second different coding region, outside the cell, and then re-introduced into a host filamentous fungus using an appropriate vector. Then the host cells express the protein of the second coding region, under the control of the introduced promoter region. The second coding region may be one that is foreign to the host species, such as a PKS, in which case the host will express a protein not naturally expressed by the given host. Alternatively, the second coding region may be one which is natural to the host, in which case it is associated with a promoter region different from the promoter region with which it naturally associates in the given host, to give modified or enhanced protein expression and activity.

The present invention also provides the ability to introduce foreign coding regions into fungi along with promoters to arrange for the host fungi to express different proteins. It also provides the ability to regulate transcription of the individual genes which occur naturally therein or foreign genes introduced therein, via the promoter region which has been introduced into the host along with the gene. For example, the promoter region naturally associated with the alcohol dehydrogenase I. (alcA) gene and the aldehyde dehydrogenase (aldA) genes of *A. nidulans* are regulatable by means of ethanol, threonine, or other inducing substances in the extracellular medium. This effect is dependent on the integrity of a gene known as alcR. When the alcA or aldA promoter region is associated with a different structural gene in *Aspergillus* or the like, in accordance with the present invention, similar regulation of the expression of the different genes by ethanol or other inducers can be achieved.

As a further example, the promoter region naturally associated with the glucoamylase gene in *Aspergillus niger* and used in embodiments of the present invention is positively induced with starch and other sugars.

In summary, any suitable microbial host cell can be genetically modified to make the compounds that are the subject of this invention.

Suitable promoters for use in mammalian cells, actinomycetes, plant cells, insect cells and the like are also well known to those in the art. Thus, for example, in the context of single cell plants, such as, algae or cultures of plant cells, in some embodiments, a transgene of interest can be placed into a vector with appropriate regulatory and other functional elements to ensure stability of the construct, replication of the construct. The construct elements are operatively linked to ensure function. The phrase "operatively linked" means that the elements of the construct are linked to enable function, such as, expression of the transgene. A construct can be assembled from the various components obtained as known, using techniques known in the art, such as those described in Sambrook et al. (1989, Molecular Cloning, A Laboratory Manual, Nolan, ed., New York: Cold Spring Harbor Laboratory Press).

As is known in the art, it can be beneficial to include elements that are optimized for use in the host of interest, such as, are known to operate in plant cells, such as, in algal cells. For example, a suitable plant promoter can be used. Many such plant promoters are known and include constitutive, tissue and temporally specific promoters. Examples of constitutive promoters include, but are not restricted to, octopine synthase (Ellis et al., 1987, EMBO J. 6, 11-16, nopaline synthase (Bevan et al., NAR 1983 25, 11(2):369-85), mannopine synthase (Langridge et al, PNAS, 1989, 86, 3219-3223), those derived from the T-DNA of *Agrobacterium tumefaciens*; CaMV35S (Odell et al., Nature. 1985, 313(6005):810-2) and CaMV19S (Lawton et al. Plant Mol. Biol. 9:315-324, 1987); rice actin (McElroy et al., Plant Cell, 2:163-171, 1990), maize ubiquitin (Christensen et al., 1992, Plant Mol Biol 18:675-689), sunflower ubiquitin (Binet et al., 1991, Plant Science, 79, pp 87-94) and plant histone promoters (Brignon et al., Plant J. 1993, 4(3):445-457). Examples of tissue-specific promoters, include seed-specific promoters, including, but not limited to the phaseolin promoter (Sengupta-Gopalan et al., 1985, Proc Natl Acad Sci USA 85: 3320-3324), conglycinin promoter (Beachy et al., 1985, EMBO J. 4: 3407-3053), conlinin promoter (Truksa et al, 2003, Plant Phys and Biochem 41: 141-147), oleosin promoter (Plant et al., 1994, Plant Mol Biol 25(2): 193-205), and the helianthinin promoter (Nunberg et al., 1984, Plant Cell 6: 473-486). Other promoters of interest are the *Brassica napus* napin promoter (European Pat No 0255278) which is seed-specific, the fatty acid elongase promoter (WO2/052024), promoters for plant ACP genes (U.S. Pat. No. 5,420,034), promoters for desaturase genes (Thompson et al. (Proc. Nat. Acad. Sci. (1991) 88:2578-2582)), from a Bce-4 gene (U.S. Pat. No. 5,530,194) or the 5' regulatory region associated with the plant synthase structural gene.

Transcription termination regions also can be used, such as that found immediately 3' downstream to the plant synthase structural gene. As with other eukaryotic organisms described herein, introns, splice sites and other elements known in the art can be used to facilitate desirable properties.

A gene of interest can be introduced into a cell of interest in a variety of means. For example, a transgene per se can be introduced directly, such as using particles coated with the transgene of interest. Bacterial cloning vectors can be used. Alternatively, *Agrobacterium*-based systems can be used, see, for example, EP-B-0 116 718 or EP-B-0 120 516. Also, protoplast transformation using calcium, polyethylene glycol or electroporation, microinjection, using silicon carbide fibres and so on can be used, as known in the art.

Selectable markers suitable for use in bacteria such as *E. coli* and actinomycetes generally impart antibiotic resistance; those for use in yeast often complement nutritional requirements. Selectable markers for use in yeast include, but are not restricted to URA3, LEU2, LEU2-d, TRP1, LYS2, HIS1, HIS3. Selectable markers for use in actinomycetes include, but are not restricted to those for thiostrepton-, apramycin-, hygromycin-, and erythromycin-resistance.

Methods and materials for construction of vectors, transformation of host cells and selection for successful transformants are well understood in the art.

Thus, according to one embodiment of the invention herein, a single host cell will be modified to contain one or a multiplicity of vectors, each vector contributing a portion of the synthesis of the final product. In constructing multiple vectors for production of aromatic compounds, the separate reading frames may be incorporated on separate vectors or, if properly constructed, portions of reading frames can be distributed among more than one vector, each with appropriate sequences for effecting control of expression or alternatively, they may be integrated into the chromosomes to contribute to the synthesis of the final product. Indeed, all genes, encoding all the enzymes for a certain product (i.e. an operon), may be incorporated into the genome of an industrial organism. Furthermore, that operon may be designed to be "portable", such that DNA encoding the operon may be rapidly tested in additional strains and organisms for optimal production of the desired product at industrial scale.

Alternatively, two or more enzymes may be expressed from one or more plasmids or chromosomally-integrated DNA, using di- and/or multi-cistronic message constructs. In such constructs, open reading frames may be separated by internal ribosome entry sites (IRESs) allowing efficient translation of all open reading frames on the messenger RNA. In yeast, useful IRES sequences from *S. cerevisiae* have been described, and these have also been shown to function efficiently in the methylotrophic yeast *P. pastoris* (gra103.aca.ntu.edu.tw/gdoc/98/D92B47403a.pdf).

In one other aspect, the present invention provides expression systems comprising at least one IRES. In one embodiment, the open reading frames of two or more of the following are separated by one or more IRESs: i) at least one nucleotide sequence that encodes an aromatic polyketide synthase (PKS) for 6-methylsalicylic acid (6-MSAS) or an orsellinic acid synthase (OSAS); ii) at least one nucleotide sequence that encodes a holo acyl carrier protein (ACP) synthase; and iii) at least one nucleotide sequence that encodes a decarboxylase.

As stated herein, one or more or all of the above expression systems introduced into the host may be integrated into the chromosome or expressed from a yeast artificial chromosome (YAC).

Integration can be effected, for example, using homologous recombination. If homologous recombination is used, the integration may also delete endogenous PKS activity ordinarily residing in the chromosome, as described in the above-cited PCT application WO 95/08548. In these embodiments too, a selectable marker such as hygromycin or thiostrepton resistance will be included in the vector that effects integration.

As described above, additional enzymes which effect post-translational modifications to the enzyme systems in the PKS may need to be introduced into the host through suitable recombinant expression systems. In addition, enzymes that convert the polyketides themselves, for example, through decarboxylation, methylation, or glycosylation may be needed. It may also be necessary to modify the catalytic domains to alter their substrate specificity or to substitute domains with the appropriate specificity and catalytic activities. For example, malonyl CoA levels in yeast may be enhanced by incorporation, into the yeast host, expression systems for enhanced synthesis of malonyl-CoA, such as an overexpressed gene for malonyl CoA synthase, or for acetyl CoA carboxylase as described in Wattanachaisaer-eekul et al., Metab Eng 10, 246-54, 2008.

In other embodiments of the invention normal cellular metabolic processes may be enhanced or deleted to maximize production of the cresol, orcinol or cresol-orcinol-ether products. For example, to divert carbon flux away from the production of ethanol and towards the production of the desired product, expression of one or more enzymes in the ethanol producing pathway may be knocked out or reduced in activity through genetic manipulation. In one specific embodiment, the activity of pyruvate decarboxylase may be knocked out completely or reduced by gene deletion or disruption. In another, the ADH1 gene may be similarly modified.

Thus, the present invention provides the opportunity to enhance the production of polyketide-derived molecules in hosts that have the basic machinery to make polyketides, but to further direct the production of molecules that can be used directly as specialty chemical precursors, an energy source, or can be modified or converted into an energy source. The invention also provides more efficient means to provide a variety of products by supplying the elements of the introduced PKS along with the activities of modification enzymes to make even more desirable products in situ.

In a preferred embodiment of the invention, the PKS gene is fused in-frame to one or more modification enzyme genes. For example, a 6-MSAS or KR-deleted 6-MSAS/decarboxylase fusion protein wherein both enzymes are active is used to convert sugars to m-cresol or orcinol directly via the glycolytic pathway. A trifunctional enzyme complex derived from the above, that also contains a fusion gene-encoded O-methyltransferase can be expressed, thereby, taking sugar, via pyruvate to a methylanisole or a dimethoxytoluene directly.

Petroleum-derived fuels, such as gasoline, aviation gasoline, kerosene, jet fuel and so on are mixtures of compounds suitable for use in a combustion setting. Generally, such classifications relate to compounds obtained by fractional distillation of crude oil based on temperature ranges. Hence, gasoline generally contains hydrocarbons (HCs) from $C_5$ to $C_{12}$ in length obtained at about the 150° range, kerosene, which includes jet fuels, contains HCs from $C_{12}$ to $C_{15}$ in length obtained at about the 200° range and so on. Diesel fuel has a density of about 0.85 kg/l, about 15% more than that of gasoline. Diesel generally contains about 75% paraffins, both linear and cyclic, and 25% aromatics. Generally the molecules have from 10 to 15 carbons. Biodiesel generally comprises methyl esters instead of alkanes and aromatic hydrocarbons, as many are obtained by partially degrading triglycerides to yield fatty acids and fatty acid esters. Aromatic compounds and cyclohexane derivatives from the present invention may be used directly as blending agents for the above fuels or, alternatively, may be starting materials for esterification and etherification with alkyl groups of the appropriate length for the fuel characteristics required.

In some embodiments, a first enzyme of the engineered metabolic pathway may be under the control of a first promoter and the second enzyme of the engineered pathway may be under the control of a second promoter, wherein the first and the second promoter have different strengths. For example, the first promoter may be stronger than the second promoter or the second promoter may be stronger than the first promoter. Consequently, the level a first enzyme may be increased relative to the level of a second enzyme in the engineered pathway by increasing the number of copies of the first enzyme and/or by increasing the promoter strength to which the first enzyme is operably linked relative to the promoter strength to which the second enzyme is operably linked. In some other embodiments, the plurality of enzymes of the engineered pathway may be under the control of the same promoter.

In one aspect, the present invention provides modified recombinant host cells and methods for the production of a methylated phenolic compound in which a promoter is used to control expression of one enzymatic component within the cell. During the process of making a methylated phenolic compound, the rate of biosynthesis of a phenolic compound typically exceeds the rate of methylation of the phenolic compound. For example, the rate of biosynthesis of m-cresol or orcinol from the cells and methods described herein exceeds the rate of methylation of m-cresol or orcinol by an O-methyltransferase. As a result, the overproduction of m-cresol or orcinol can cause toxicity problems for the cells. In one embodiment, the present invention provides a modified recombinant host cell comprising an expression system for a decarboxylase wherein expression of the decarboxylase is controlled by a promoter that reduces the expression of the decarboxylase. In one embodiment, the promoter is the Leu2d promoter. Leu2d is known to be partially defective. In another embodiment, the host cell with the promoter for reduced decarboxylase expression is capable of producing a methylated phenolic compound, such as 3-methylanisole or 3,5 dimethoxytoluene. In one other embodiment, the decarboxylase with reduced expression due to the promoter is a 6-MSA decarboxylase expressed from the PatG gene of *Aspergillus clavatus*.

In other embodiments, altering the ribosomal binding site affects relative translation and expression of different enzymes in the pathway. Altering the ribosomal binding site can be used alone to control relative expression of enzymes in the pathway, or can be used in concert with the aforementioned promoter modifications and codon optimization that also affect gene expression levels.

In an exemplary embodiment, expression of the potential pathway enzymes may be dependent upon the presence of a substrate on which the pathway enzyme will act in the reaction mixture. For example, expression of an enzyme that catalyzes conversion of A to B may be induced in the presence of A in the media. Expression of such pathway enzymes may be induced either by adding the compound that causes induction or by the natural build-up of the compound during the process of the biosynthetic pathway (e.g., the inducer may be an intermediate produced during the biosynthetic process to yield a desired product).

In some embodiments, computer-implemented design techniques may be used to generate alternative pathways for generating an organic molecule of interest. In some embodiments, the databases contain information on genome and their link may be utilized for designing novel metabolic pathways. Examples of database are MetaCyc (a database of metabolic pathways and enzymes, the University of Minnesota biocatalysis/biodegradation database (a database of microbial catalytic reactions and biodegradation pathways for organic chemical compounds), LGAND (a composite database that provides information about metabolites and other chemical compounds, substrate-product relations representing metabolic and other reactions and information about enzyme molecules). A database of pathway components may also contain components of predicted, putative, or unknown functions. It may also contain pseudo-components of defined function that may have an undefined composition. In some embodiments, a program may design combinations of regulatory and/or functional elements that are in the public domain (e.g., that are not covered by patent rights and/or are not subject to a licensing fee). Databases of freely available genetic elements may be generated and/or used as a source of nucleic acid sequences that can be combined to produce alternative pathways. Alternative pathways containing different combinations of known functional and/or regulatory elements (e.g., from different species) may be designed, assembled, and/or tested. Libraries including variations in enzymatic element regions may be used to ascertain the relative effects of different types of enzymes or of different variants of the same enzyme. Libraries including variations in regulatory element regions may be used to ascertain the optimal expression level or regulatory control among a set of genes.

Nucleic acids encoding the different pathways may be assembled. In some embodiments, the functional properties of different engineered pathways may be tested in vivo by transforming host cells or organisms with the appropriate assembled nucleic acids, and assaying the properties of the engineered organisms. In some embodiments, the functional properties of different engineered pathways may be tested in vitro by isolating components expressed from assembled nucleic acids and testing the appropriate combinations of components in an in vitro system.

In some embodiments of the present invention, haploid yeast strains of yeast may be used. In others, diploid strains are preferred. They may be modified laboratory strains, or industrial strains, or modified industrial strains. Renewable feedstocks for yeast growth may be derived from purified or partially purified sugars from corn, wheat, sugar cane, sugar beets, and so on, or from cellulosic sources such as wood, switch grass, bamboo, jatropha and so on. They may also be derived from microalgae, cyanobacteria and similar organisms that can produce sugars from carbon dioxide and sunlight.

Production of Compounds

As exemplified in the Table 1 below, the modified recombinant host cells and methods described herein allow for the production and isolation of numerous compounds of interest.

TABLE 1

| Enzymes expressed in a host cell system | Capable of production & isolation from cell | Process step outside the cell | Produced outside the cell |
|---|---|---|---|
| PKS + ACPS | 6-MSA/HMBA | | |
| PKS + ACPS | 6-MSA/HMBA | metal catalyst | m-cresol |
| PKS + ACPS + DC | m-cresol | | |
| PKS* (or OSAS) + ACPS | OSA | | |
| PKS* (or OSAS) + ACPS + DC | orcinol | | |
| PKS + ACPS + DC | m-cresol | alkylation | 3-methylanisole |
| PKS* (or OSAS) + ACP + DC | orcinol | alkylation | 3,5-dimethoxytoluene |
| PKS + ACPS + DC + OOMT | 3-methylanisole | | |
| PKS* (or OSAS) + ACPS + DC + OOMT | 3,5-dimethoxytoluene | | |
| PKS + ACPS | 6-MSA/HMBA | oxidation | 3-hydroxyphthalic anhydride |

PKS - PKS for for 6-MSA (6-MSAS)
PKS* - modified PKS for 6-MSA (6-MSAS) with an inactive KR domain 1. 6-MSA or OSA In one aspect, the present invention provides modified recombinant cells and methods for the production of 6-methylsalicylic acid (6-MSA) or orsellinic acid (OSA). In one embodiment, the modified recombinant cell comprises a first expression system at least one nucleotide sequence that encodes an aromatic polyketide synthase (PKS) for 6-methylsalicylic acid (6-MSAS) or an orsellinic acid synthase (OSAS), capable of being expressed. In another embodiment, the host cell further comprises a second expression system that comprises at least one nucleotide sequence that encodes a holo acyl carrier protein (ACP) synthase. In one other embodiment, the ACP synthase pantetheinylates said PKS. In one other aspect, the host cell expresses an aromatic PKS for 6-MSA (6-MSAS). In one embodiment, the aromatic PKS is the synthase for 6-MSA (6-MSAS) from a fungus. In another embodiment, the aromatic PKS is the synthase for 6-MSA (6-MSAS) from a prokaryote. In one other embodiment, the synthase for a prokaryotic 6-MSAS is encoded by the ChlB1 gene from *S. antibioticus* in wild-type form. In some embodiments, the aromatic PKS is the synthase for the OSAS. In one embodiment, the OSAS is encoded by the AviM gene from *Streptomyces viridochromogenes*.

In another embodiment, the synthase for a prokaryotic 6-MSAS comprises an inactivated ketoreductase (KR) domain such that orsellinic acid (OSA) is produced by the cell. In preferred embodiments, the 6-MSA and OSA are intermediate compounds, e.g., phenolic or phthalic anhydride intermediate compounds as described herein.

In one aspect, the present invention contemplates use of bacterial iterative PKSs. In one embodiment, the bacterial iterative PKS is selected from the group consisting of *Streptomyces antibioticus* DQ116941 ChLB1; *Streptomyces pactum* AB303063 pctS; *Actinomadura madurae* AY271660 6-MSA); *Frankia* sp. NC 009921; *Salinispora arenicola* NC 009953 a; *Micromonospora echinospora* AF505622 CalO5; *Streptomyces viridochromogenes* AF333038 AviM; *Salinispora arenicola* NC 009953 b; *Streptomyces carcinostaticus* AY117439 NcsB; *Saccharopolyspora erythraea* NC 009142; and *Mycobacterium tuberculosis* NC 000962 ppsA.

6-MSAS genes may be obtained from any natural source, such as fungi, bacteria or plants, or may be synthetic, hybrid or modified derivatives that lead to optimized biosynthetic characteristics of the expressed 6-MSAS PKS. In one embodiment, the 6-MSAS gene used may be derived from plants such as the narrow-leaf yerba-santa (*Eriodyction pavonina*), Khaden S, and Marles, R J. Molecules 15; 7985-8005 (2010). Modification and optimization of enzymatic activities are well known to those skilled in the art.

In another variation, one or more expression systems for a defined portion of a PKS system are integrated into the host chromosome and at least one additional expression system resides on a replicable vector. Thus, in the case of 6-MSAS or OSAS, an expression system for one of the open reading frames may first be integrated into the chromosome and expression systems for other open reading frames may reside on vectors. The integration of such expression systems into the chromosome can occur either through known methods and means.

In one embodiment, the present invention provides a modified recombinant host cell comprising a first expression system for 6-MSAS (or OSAS) and/or a second expression system for holo ACP synthase integrated into the host chromosome. In another embodiment, the modified host cell comprises a first expression system for 6-MSAS (or OSAS) integrated into the host chromosome and a second expression system for holo ACP synthase present in the cell on a replicable vector. In one embodiment, the modified host cell comprises a first expression system for 6-MSAS (or OSAS) present in the cell on a replicable vector and a second expression system for holo ACP synthase integrated into the host chromosome.

In another aspect, 6-MSA and OSA are each capable of being produced and/or isolated by the modified recombinant host cells and methods described herein. Once produced by and isolated from the cells, 6-MSA and OSA can serve as compound intermediates for the production of compounds of interest (e.g., m-cresol; 3-methylanisole; 3,5-dimethoxytoluene; phthalic anhydride, etc.).

2. m-Cresol or Orcinol

In another aspect, the present invention provides modified recombinant cells and methods for the production of m-cresol or orcinol. In one embodiment, the modified recombinant host cell comprises a first and second expression system, as described in the section above. In another embodiment, the cell further comprises a third expression system that includes at least one nucleotide sequence encoding a decarboxylase.

In one embodiment, the present invention provides a modified recombinant host cell comprising a first expression system for 6-MSAS (or OSAS) and/or a second expression system for holo ACP synthase integrated into the host chromosome. In another embodiment, the modified host cell further comprises a third expression system for a decarboxylase that is present in the cell on a replicable vector. In one other embodiment, the modified host cell further comprises a third expression system for a decarboxylase that is integrated into the host chromosome. In one embodiment, the host cell comprises at least one of the expression systems for 6-MSAS (or OSAS), holo ACP synthase, and decarboxylase integrated into the host chromosome; and at least one of the same expression systems present on a replicable vector. In another embodiment, the host cell comprises all of the expression systems for 6-MSAS (or OSAS), holo ACP synthase, and decarboxylase integrated into the host chromosome; or all of the same expression systems present on a replicable vector.

In one embodiment, the decarboxylase nucleotide sequence is selected from the group consisting of the 6-MSA decarboxylase gene from *P. patulum*, the PatG gene from *Aspergillus clavatus* or the OSA decarboxylase gene from *Gliocladium roseum*, the 2,3-dihydroxybenzoic acid decarboxylase genes from *Aspergillus* species, and the 5-carboxyvanillate decarboxylase gene from *Sphingomonas paucimobilis* SYK-6. In another embodiment, the product capable of being produced by and isolated from the host cell is m-cresol or orcinol.

In another specific embodiment, the invention relates to a cell modified to produce m-cresol or orcinol via in vivo or ex vivo decarboxylation. In the former cell line, a decarboxylase specific for 6-MSA (HMBA) or orsellinic acid is expressed from a natural or modified decarboxylase gene within the same cell. Natural decarboxylase genes include the 6-MSA decarboxylase gene from *P. patulum*, the PatG gene from *Aspergillus clavatus*, and the orsellinic acid decarboxylase gene from *Gliocladium roseum* (Pettersson et al., 1965; *Acta Chem. Scand.* 19: 2013-2021). It should also be understood that other decarboxylase genes encoding product enzymes with substrate specificities for closely or even distantly related aromatic carboxylic acids can be modified by mutation or selective breeding to also produce effective decarboxylating enzymes.

In another aspect, two different types of modified recombinant host cells are employed to produce a compound of interest. In one embodiment, the present invention provides a first cell comprising a first PKS (6-MSAS or OSAS) expression system and a second holo ACP synthase expression system, and a second cell comprising a third decarboxylase expression system. In another embodiment, the first PKS expression system and/or the second holo ACP synthase expression system is integrated into the chromosome of the first cell, or present in the first cell on a replicable vector. In one other embodiment, the third expression system for the decarboxylase is integrated into the chromosome of the second cell, or present in the second cell on a replicable vector.

In one aspect, the present invention provides a mixture of modified recombinant host cells for the production of a compound of interest. In one embodiment, the mixture comprises a first modified recombinant host cell containing i) a first expression system that comprises at least one nucleotide sequence that encodes an aromatic polyketide synthase (PKS) for 6-methylsalicylic acid (6-MSAS), capable of being expressed, and ii) a second expression system that comprises at least one nucleotide sequence that encodes a holo acyl carrier protein (ACP) synthase, wherein the ACP synthase pantetheinylates said PKS; and a second modified recombinant host cell containing iii) a third expression system that comprises at least one nucleotide sequence that encodes a decarboxylase. In another embodiment, the mixture is a co-cultivated mixture of the first and second modified recombinant host cells. In one other embodiment, the first modified recombinant host cell is a yeast cell. In another embodiment, the yeast cell is a *S. cerevisiae* cell. In one other embodiment, the second modified recombinant host cell is a fungal cell. In another embodiment, the fungal cell is *A. clavatus*. In an additional embodiment, the present invention provides a method of co-cultivation of the first modified recombinant host cell and the second modified recombinant host cell that results in the production of a phenolic compound. In one embodiment, the phenolic compound is m-cresol. This method is exemplified in Example 6.

3. 3-methylanisole and 3,5 dimethoxytoluene

In one other aspect, the present invention provides modified recombinant cells and methods for the production of methylated phenolic compounds. In one embodiment, in addition to the first (e.g., PKS), second (e.g., holo ACP synthase), and third (e.g., decarboxylase) expression systems described herein, the methods and cells comprise a fourth or additional expression system for a heterologous O-methyltransferase (OMT). Such modified recombinant cells and methods utilizing an expression system for an OMT provide for the production of 3-methylanisole or 3,5-dimethoxytoluene.

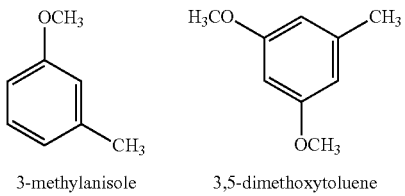

3-methylanisole     3,5-dimethoxytoluene

In another embodiment, the additional expression system is included in the vectors, chromosomes or YACS, such that the isolated products are 3-methylanisole or 3,5-dimethoxytoluene. In one other embodiment, the O-methyltransferase is selected from the OOMT1, OOMT2, OOMT3, OOMT4, COMT1 genes of *Rosa chinensis* varietal and hybrid strains of rose.

In one aspect, the present invention provides modified recombinant cells and methods for the production of methylated phenolic compounds, e.g., 3-methylanisole or 3,5-dimethoxytoluene. In one embodiment, the modified recombinant cell comprises a first expression system at least one nucleotide sequence that encodes an aromatic polyketide synthase (PKS) for 6-methylsalicylic acid (6-MSAS) or an orsellinic acid synthase (OSAS), capable of being expressed. In another embodiment, the host cell further comprises a second expression system that comprises at least one nucleotide sequence that encodes a holo acyl carrier protein (ACP) synthase. In one other embodiment, the ACP synthase pantetheinylates said PKS. In another embodiment, the cell further comprises a third expression system that includes at least one nucleotide sequence encoding a decarboxylase.

In one other aspect, the host cell expresses an aromatic PKS for 6-MSA (6-MSAS). In one embodiment, the aromatic PKS is the synthase for 6-MSA (6-MSAS) from a fungus. In another embodiment, the aromatic PKS is the synthase for 6-MSA (6-MSAS) from a prokaryote. In one other embodiment, the synthase for a prokaryotic 6-MSAS is encoded by the ChlB1 gene from *S. antibioticus* in wild-type form. In some embodiments, the aromatic PKS is the synthase for the OSAS. In one embodiment, the OSAS is encoded by the AviM gene from *Streptomyces viridochromogenes*. In another embodiment, the synthase for a prokaryotic 6-MSAS comprises an inactivated ketoreductase (KR) domain such that orsellinic acid (OSA) is produced by the cell.

In preferred embodiments, host cells and methods described herein result in the production of m-cresol as a phenolic compound intermediate for 3-methylanisole; or orcinol as a phenolic compound intermediate for 3,5-dimethoxytoluene. In another embodiment, the method comprise isolating m-cresol or orcinol from the host cells and treating with a methylating agent to form 3-methylanisole or 3,5-dimethoxytoluene, respectively.

In another aspect, the present invention provides modified recombinant host cells and methods for producing methylated phenolic compounds directly from the host cells. In one embodiment, the present invention provides a cell comprising a first PKS expression system, a second holo ACP synthase expression system, and a third decarboxylase expression system, which comprises a further expression system for a methyltransferase. In a further embodiment, a further expression system containing a nucleotide sequence encoding at least one O-methyltransferase gene operably linked to a promoter operable in said cell is included, allowing the production and isolation of methyl ethers of the aromatic polyketide products. The O-methyltransferase genes and their progeny that are modified for enhanced catalytic activities or tighter substrate specificity, may be obtained from multiple sources. For example, in a preferred embodiment, the orcinol O-methyltransferase OOMT1 from rose petals is utilized for the transformation. The O-methyltransferase DNA sequences may be obtained from the following sources, but is not limited to just these sources: *Rosa Chinensis, R. rugosa, R. majalis, R. beggeriana, R. odorata, R. canina, R. gallica, r. woodsii, R. marettii, R. roxburghii, Vitis vinifera, Humulus lupulus, Prunus dulcis,* and *Prunus armeniaca*.

In one embodiment, the present invention provides a modified recombinant host cell comprising a first expression system for 6-MSAS or OSAS, capable of being expressed, and/or a second expression system for holo ACP synthase integrated into the host chromosome. In another embodiment, the modified host cell further comprises a third expression system for a decarboxylase and/or an OMT that is present in the cell on a replicable vector. In one other embodiment, the modified host cell further comprises a third expression system for a decarboxylase and/or an OMT that is integrated into the host chromosome. In one embodiment, the host cell comprises at least one of the expression systems for 6-MSAS (or OSAS), holo ACP synthase, decarboxylase, and OMT integrated into the host chromosome; and at least one of the same expression systems present on a replicable vector. In another embodiment, the host cell comprises all of the expression systems for 6-MSAS (or OSAS), holo ACP synthase, decarboxylase, and OMT integrated into the host chromosome; or all of the same expression systems present on a replicable vector.

In a further embodiment, overexpression of genes encoding various methylenetetrahydrofolate reductases (MTHFRs) or MTHFR fusion proteins may be used to keep an elevated supply of S-adenosylmethionine available as a substrate for the O-methyltransferase reaction, as described by Roje et al., J. Biol Chem 277; 4056-4061 (2002). In one embodiment, the modified recombinant host cells and methods of using the same could employ a fifth expression system comprising at least one nucleotide sequence encoding a MTHFR, such that S-adenosylmethionine is produced in the cell. In another embodiment, the modified recombinant host cell comprises a first PKS expression system, a second holo ACP synthase expression system, a third decarboxylase expression system, a fourth OMT expression system, which comprises a further expression system for a methylenetetrahydrofolate reductase.

In another aspect, the present invention provides a method of producing and isolating a phenolic compound intermediate from a host cell. In one embodiment, the method comprises providing a modified recombinant host cell comprising i) a first expression system that comprises at least one nucleotide sequence encoding an aromatic polyketide synthase (PKS) for 6-methyl salicylic acid (6-MSAS), capable of being expressed; ii) a second expression system that comprises at least one nucleotide sequence encoding a holo acyl carrier protein (ACP) synthase, wherein the ACP synthase pantetheinylates said PKS; and iii) a third expression system that comprises at least one nucleotide sequence that encodes a decarboxylase. In another embodiment, the method further comprises the step of isolating the phenolic compound intermediate produced in the recombinant host cell. In one other embodiment, the method further comprises alkylating the phenolic compound intermediate obtained in the isolating step to form an alkylated phenolic compound by treating with a alkylating agent. Alkylating agents include any agent capable of adding an alkyl group to a substrate, including agents that facilitate the replacement of a hydrogen atom with an alkyl group. In some embodiments, the alkylating agent is selected from the group consisting of ethanol, methanol, isopropanol, butanol, and the like. In another aspect, the method comprises treating a compound intermediate isolated from a cell with an alkylating agent to provide one of the following alkyl group: ethyl, methyl, isopropyl, tertiary butyl, and the like, to the compound intermediate.

In one embodiment, the phenolic compound intermediate is m-cresol, which is then treated with an alkylating agent to produce an alkylated phenolic compound. In one embodiment, the alkylating agent is ethanol to produce 3-ethylanisole; methanol to produce 3-methylanisole; isopropanol to produce 3-isopropylanisole; or tert-butanol to produce 3-butylanisole. In one embodiment, the alkylating agent is a methylating agent selected from methanol, methyliodide, dimethyl carbonate. In another embodiment the methylation is O-methylation.

In one embodiment, the phenolic compound intermediate is orcinol, which is then treated with an alkylating agent to produce an alkylated phenolic compound. In one embodiment, the alkylating agent is ethanol to produce 3,5-diethoxytoluene; methanol to produce 3,5-dimethoxytoluene; isopropanol to produce 3,5-diisoproxytoluene; or tert-butanol to produce 3,5-dibutoxytoluene. In one embodiment, the alkylating agent is a methylating agent selected from methanol and dimethyl carbonate. In another embodiment the methylation is O-methylation.

4. Phthalic Anhydride

In one aspect, the present invention provides modified recombinant cells and methods for the production of phthalic anhydride compounds. In one embodiment, the compound is 3-hydroxyphthalic anhydride.

In one embodiment, the modified recombinant cell comprises a first expression system at least one nucleotide sequence that encodes an aromatic polyketide synthase (PKS) for 6-methylsalicylic acid (6-MSAS), capable of being expressed. In another embodiment, the host cell further comprises a second expression system that comprises at least one nucleotide sequence that encodes a holo acyl carrier protein (ACP) synthase. In one other embodiment, the ACP synthase pantetheinylates said PKS. The PKS and ACP components may vary as described herein.

In another aspect, the present invention provides a method of producing a phthalic anhydride compound. In one embodiment, the method comprises providing a modified recombinant host cell comprising i) a first expression system that comprises at least one nucleotide sequence encoding an aromatic polyketide synthase (PKS) for 6-methyl salicylic acid (6-MSAS), capable of being expressed; and ii) a second expression system that comprises at least one nucleotide sequence encoding a holo acyl carrier protein (ACP) synthase, wherein the ACP synthase pantetheinylates said PKS. In another embodiment, the method further comprises the step of isolating a phthalic anhydride intermediate compound produced in the recombinant host cell. In one other embodiment, the method further comprises oxidizing the phthalic anhydride intermediate compound obtained in the isolating step to form the phthalic anhydride compound by treating with an oxidizing agent. Oxidizing agents include any agent capable of facilitating the removal. In some embodiments, the oxidizing agent is air, including ambient air. Those of ordinary skill in the art will appreciate other oxidizing agents that are suitable for use in the present invention. In one embodiment, the phthalic anhydride intermediate compound is 6-MSA.

4. Expression Systems

The invention herein employs expression systems for the catalytic activities involved in an aromatic PKS system for the production of specialty chemicals of the cresol, anisole, toluene, cyclohexane, cyclohexanol and other six-membered ring compound families. These are petroleum-based fuel compatible molecules, such as 3-methylanisole (see, for example U.S. Pat. No. 4,407,661) or 3-ethoxytoluene, 3-isopropoxytoluene, or m-cresol etherified with glycerol, and the corresponding dialkylated orcinol derivatives. The proteins produced may contain the native amino acid sequences and thus the substrate specificities and activities of the native forms, or altered forms of these proteins may be used so long as the desired catalytic activity is maintained. The specificity and efficiency of this activity may, however, differ from that of the native forms. Certain activities present in the native system, however, can be intentionally deleted or inactivated, such as by inactivating the ketoreductase (KR) domain of a 6-MSAS gene to generate an enzyme with OSAS activity (see, for example Ding et al., Chem Biol 17:495-503, 2010). Further, components of various aromatic systems can be mixed and matched, as well as can components of various modules of the modular systems. PCT application WO 95/08548, incorporated herein by reference, describes the construction of hybrid aromatic PKS systems where, for example, open reading frames of actinorhodin are included in expression vectors with open reading frames from alternative aromatic systems.

Expression systems for the PKS proteins alone may not be sufficient for actual production of polyketides unless the recombinant host also contains holo ACP synthase activity which effects pantetheinylation of the acyl carrier protein. This activation step is necessary for the ability of the ACP to "pick up" the 2-carbon unit that is the starter unit or the growing polyketide chain in the series of Claisen condensations which result in the finished polyketide. For hosts lacking a phosphopantetheinylating enzyme that behaves as a holo ACP synthase, the invention provides means for conferring this activity by supplying suitable expression systems for this enzyme. The expression system for the holo ACP synthase may be supplied on a vector separate from that carrying a PKS unit or may be supplied on the same vector or may be integrated into the chromosome of the host, or may be supplied as an expression system for a fusion protein with all or a portion of a polyketide synthase. In general, holo ACP synthases associated with fatty acid synthesis are not suitable; rather, synthases associated specifically with polyketide synthesis or with synthesis of nonribosomal proteins are useful in this regard. Certain holo ACP synthases, however, that are associated with fatty acid synthesis, e.g. the npgA protein of *Aspergillus nidulans*, have been shown to function in the biosynthesis of polyketides in heterologous hosts, such as yeast (Wattanachaisaereekul et al., Biotech Bioeng 97: 893-900, 2007).

Specifically, the modular PKS systems are not activated by phosphopantetheinylation resulting from the phosphopantetheinylation enzymes endogenous to certain host cells, such as, *E. coli*; however, enzymes derived from *Bacillus*, in particular the gramicidin holo ACP synthase of *Bacillus brevis*, the surfactin-related holo-ACP synthase from *Bacillus subtilis*, and the fatty acid synthesis-associated npgA PPTase protein from *Aspergillus nidulans* can utilize the modular PKS ACP domains as substrates. Similarly, npgA has been shown to also be capable of activating the iterative, aromatic PKS 6-MSAS. While inclusion of an expression system for an appropriate holo-ACP synthase is not necessary for just the expression of the genes encoding modular PKS or yeast or other eukaryotes, inclusion of such expression systems may be required if polyketides and their derivatives are to be produced by the expressed enzymes.

In another aspect, the expression systems in the host cell may be provided on one or more vectors. In one embodiment, the first expression system for the PKS and the second expression system for the holo ACP synthase, are present on the same vector, are present on separate vectors, or are expressed from a dicistronic messenger RNA. In another embodiment, the third expression system for a functional decarboxylase is present on the same vector as the PKS and/or holo ACP synthase, or is present on a separate vector. In one other embodiment, the first expression system for the PKS and the second expression system for the holo ACP synthase and the third expression system for a functional decarboxylase are present on the same vector. In some embodiments, one or more of (or all) the first, second, and third expression systems are integrated into the host cell chromosome or expressed from yeast artificial chromosomes (YACs). In one other embodiment, wherein at least two (or all three) of the expressed PKS, holo ACP synthase and decarboxylase are derived from a multicistronic messenger RNA.

Thus, in one aspect, the invention relates to a recombinant host cell where the host cell is modified to contain at least two vectors, a first vector containing a first selection marker and a first expression system and the second vector containing a second selection marker and a second expression system and optionally additional vectors containing additional selectable markers and expression systems, wherein the expression systems contained on the vectors encode and are capable of producing at least a minimal PKS system. If the minimal PKS system is an aromatic system, the minimal system will comprise a ketosynthase/acyl transferase (KS/AT) catalytic region, catalytic region and an acyl carrier protein (ACP) activity. In one embodiment, the host cell is selected from the group consisting of a bacterial, yeast, filamentous fungal, plant, algal, or microalgal host cell.

In one specific embodiment of this aspect of the invention, the recombinant host cell is modified to contain: (a) a first vector comprising a first selectable marker and an expression system comprising a nucleotide sequence encoding a 6-methylsalicylic acid synthase (6-MSAS) gene or an orsellinic acid synthase (OSAS) gene and; (b) a second vector comprising a second selectable marker and an expression system comprising a nucleotide sequence encoding a holo ACP synthase; and (c) a third vector containing a third selectable marker and an expression system which comprises a nucleotide sequence encoding a decarboxylase activity operably linked to a promoter operable in said cell. Alternatively, at least two of the vectors can be combined so that the host cell contains only two vectors, or even one vector; the vector containing two expression systems may maintain these as separate expression systems or two or three open reading frames may be placed under the control of a single promoter, wherein either di- or tri-cistronic messages are transcribed for translation into the designed enzymatic pathway. In other embodiments, expression systems for each and all parts of the engineered enzymatic pathway may be integrated into the host cell chromosomes. For example, the holo ACP synthase gene, npgA of *Aspergillus nidulans*, functions effectively when integrated into the *S. cerevisiae* genome (Ma et al., Science 326: 589-592 (2009).

In one other aspect, the modified recombinant host cell comprises at least one expression system that includes one or more of the following: i) at least one nucleotide sequence that encodes an aromatic polyketide synthase (PKS) for 6-methylsalicylic acid (6-MSAS) or an orsellinic acid synthase (OSAS); ii) at least one nucleotide sequence that encodes a holo acyl carrier protein (ACP) synthase; and iii) and at least one nucleotide sequence that encodes a decarboxylase.

In one embodiment, the host cell comprises a first expression system that includes at least one nucleotide sequence that encodes an aromatic polyketide synthase (PKS) for 6-methylsalicylic acid (6-MSAS) or an orsellinic acid synthase (OSAS); and at least one nucleotide sequence that encodes a holo acyl carrier protein (ACP) synthase. In another embodiment, the host cell further comprises a second expression system that includes at least one nucleotide sequence that encodes a decarboxylase.

In another aspect, the present invention provides host cells that express fusion proteins of an aromatic polyketide synthase (PKS) for 6-methylsalicylic acid (6-MSAS) or an orsellinic acid synthase (OSAS); a holo acyl carrier protein (ACP) synthase; and a decarboxylase. Such "triple fusion proteins" may be expressed by the methods described herein.

5. Host Cells

In one aspect, the present invention provides modified recombinant host cells for the production of polyketides that provide advantages over the prior art. U.S. Pat. No. 6,033,833 discloses modified recombinant host cells that use a nucleotide sequence encoding a fusion protein of PKS (modular or fungal) and holo ACP synthase. U.S. Pat. No. 6,258,566 discloses modified recombinant host cells that utilize a modular or a fungal PKS. U.S. Pat. No. 7,078,233 discloses modified recombinant host cells that utilize a modular or a fungal PKS, and an ACP synthase that is not associated with fatty acid synthesis. In one embodiment, the present invention provides a recombinant host cell that does not include a nucleotide sequence encoding a fusion protein of PKS and holo ACP synthase. In another embodiment, the PKS is not a fungal PKS or a modular PKS. In one other embodiment, the PKS is an aromatic PKS. In one other embodiment, the ACP synthase is associated with fatty acid synthesis.

In one other embodiment, the host cell is selected from the group consisting of a bacterial, yeast, filamentous fungal, plant, algal, or microalgal host cell. In one aspect, the present invention provides a variety of host cells or organisms that can be modified to produce the products contemplated by the present invention. In one embodiment, the host cell or organism *Pichia pastoris*.

In another embodiment, the host cell or organism is an *Aspergillus* species, and *Aspergillus niger*. Those of ordinary skill in the art will appreciate additional fungal species that are suitable for use in the present invention. In one embodiment, the modified host cell does not contain a heterologous expression system for a holo ACP synthase.

6. Methods of Production

In one aspect, the present invention provides method for the production of m-cresol or orcinol in a heterologous microorganism. In one embodiment, the method comprises use of a substrate for carbon flux. In another embodiment, the substrate for carbon flux is selected from the group consisting of: purified or partially purified glucose or dextrose, corn sugar, sugar cane, cellulosic sugars, such as those from wood, bamboo, switch grass or jatropha. Those of ordinary skill in the art will appreciate additional carbon sources suitable for use with the present invention. In another embodiment, the microorganism is *Pichia pastoris*.

In still another aspect, the invention is directed to methods to obtain the synthesis of supraphysiological levels of aromatic compounds in hosts. By supplying an expression system for a compatible holo ACP synthase either on a separate vector, on one of the vectors in a multiple vector system (or on a single vector for PKS expression), or as a fusion protein with a PKS or portion thereof, hosts such as, *E. coli*, yeast, filamentous fungi, algae and other microbial systems can be treated to obtain essentially an increase in copy number of the relevant genes, or other gene duplication means, in a host, or by positive regulation, such as, using inducible promoters, enhancers, and so on, obtaining enhanced transcription and/or translation and so on, enhanced levels of polyketides, cresols, orcinols and their methyl ethers can be made in convenient hosts amenable to selection and scaling for manufacturing.

In one aspect, the present invention provides modified recombinant cells and methods for obtaining high yields of the compounds of interest, including intermediates of the compounds of interest, as described herein. In one embodiment, the method comprises providing a modified recombinant yeast cell comprising i) a first expression system that comprises at least one nucleotide sequence that encodes an aromatic polyketide synthase (PKS) for 6-methyl salicylic acid (6-MSAS), capable of being expressed, and ii) a second expression system that comprises at least one nucleotide sequence that encodes a holo acyl carrier protein (ACP) synthase, wherein the ACP synthase pantetheinylates said PKS. In another embodiment, the method further comprises producing a phenol compound intermediate in the recombinant modified yeast cell. In one embodiment, the phenolic compound intermediate is 6-MSA.

The production of compounds from a microbial host cells using a PKS, e.g., 6-MSAS, has resulted in limited yields and limited efficiency with regard to the conversion of glucose. For example, Kealey et al. reported a yield of 1.7 g/L 6-MSA using a yeast host cell expressing 6-MSAS (PNAS USA, Vol. 95, pp. 505-509, January 1998), while Xie et al. reported a glucose conversion rate of 6% in a yeast host cell expressing 6-MSAS (Biotechnology and Bioengineering, Vol. 93, No. 4, Mar. 5, 2006). In a preferred embodiment, the producing step provides a yield of greater than 3 g/L of 6-MSA from a host cell expressing a PKS (see Example 1). In one other embodiment, the producing step of greater than 3 g/L of 6-MSA comprises the use of 40 g/L glucose for growth of the cells. In another embodiment, the methods described herein provide isolation of 6-MSA with greater than 60% conversion from glucose on a molar basis (see Example 1). In one embodiment, the producing step for 60% conversion comprises use of 5 g/L glucose for growth of the cells.

In accordance with the methods described herein, reaction mixtures for pathway development may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermentor, or other vessel for cell growth or incubation.

Screening may be carried out by detection of expression of a selectable marker, which, in some genetic circumstances, allows cells expressing the marker to survive while other cells die (or vice versa). Efficient screening techniques are needed to provide efficient development of novel pathways using the methods described herein. Preferably, suitable screening techniques for compounds produced by the enzymatic pathways allow for a rapid and sensitive screen for the properties of interest. Visual (calorimetric) assays are optimal in this regard, and are easily applied for compounds with suitable light absorption properties. More sophisticated screening technologies include, for instance, high-throughput HPLC-MS analysis, SPME (Solid Phase Microextraction) and GC-MS (Gas chromatography-mass spectrometry) (see Handbook of analytical derivatization reaction, D. R. Knapp; John Wiley & Sons, 1979). In some instance, screening robots are connected to HPLC-MS systems for automated injection and rapid sample analysis. These techniques allow for high-throughput detection and quantification of virtually any desired compound.

Biologically produced products of interest may be isolated from the fermentation medium or cell extract using methods known in the art. For example, solids or cell debris may be removed by centrifugation or filtration. Bioproducts of interest may be isolated by distillation, liquid-liquid extraction, membrane evaporation, adsorption, or using any methods known in the art.

In some embodiments, identification of the product of interest may be performed using an HPLC. For example, the standard samples are prepared with known amounts of the organic product in the medium (e.g. 6-MSA, OSA, m-cresol, or orcinol). The retention time of the compound or compound intermediate produced can then be compared to that of the authentic standard. In some embodiments, identification of the product of interest may be performed using a GC-MS. The resolved samples are then analyzed by a mass selective detector and compared to previous mass spectra and retention time of authentic standards.

The practice of the present methods will employ, unless otherwise indicated, conventional techniques of cell biology, cell culture, molecular biology, transgenic biology, microbiology, recombinant DNA, and immunology, engineering, robotics, optics, computer software and integration. The techniques and procedures are generally performed according to conventional methods in the art and various general references, which are within the skill of the art. Such techniques are explained fully in the literature. See, for example, Molecular Cloning A Laboratory Manual, 2.sup.nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); Lakowicz, J. R. Principles of Fluorescence Spectroscopy, New York:Plenum Press (1983), and Lakowicz, J. R. Emerging Applications of Fluorescence Spectroscopy to Cellular Imaging Lifetime Imaging, Metal-ligand Probes, Multi-photon Excitation and Light Quenching, Scanning Microsc. Suppl VOL. 10 (1996) pages 213-24, for fluorescent techniques, Optics Guide 5 Melles Griot™ Irvine Calif. for general optical methods, Optical Waveguide Theory, Snyder & Love, published by Chapman & Hall, and Fiber Optics Devices and Systems by Peter Cheo, published by Prentice-Hall for fiber optic theory and materials.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a host cell "comprising" a number of components, another embodiment would encompass a host cell "consisting essentially of" the same components, and a third embodiment would encompass a host cell "consisting of" the same components. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Expression of 6-MSAS and OSAS in *Saccharomyces cerevisiae*

Conversion of the polyketide products to m-cresol and orcinol. The *S. cerevisiae* ADH2 promoter is chemically synthesized and fused to synthetic genes for the bacterial 6-MSAS gene ChlB1 from *Streptomyces antibioticus* or the OSAS, AviM gene from *Streptomyces viridochromogenes*. A *S. cerevisiae* terminator sequence is also fused to the gene sequence, immediately subsequent to the stop codon(s) of each respective PKS gene. The expression cassette was cloned into a yeast expression vector containing the URA3 selectable marker. Similarly, a gene encoding the *A. nidulans* npgA protein is cloned into a yeast expression vector containing the selectable marker for growth in tryptophan-deficient media.

Competent *Saccharomyces cerevisiae* InvSc1 (MATa his3D1 leu2 trp1-289 ura3-52) (Invitrogen) is transformed sequentially with the expression vectors and then plated on minimal agar plates (1.7 g/L yeast nitrogen base without amino acids or ammonium sulfate (DIFCO), 5 g/L (NH$_4$)$_2$SO$_4$, 20 g/L glucose, 20 g/L agar containing amino acids for selection based on uracil and trytophan prototrophy. Transformants are picked and grown for 24 hours in uracil- and tryptophan-deficient minimal medium. Plasmid DNA is isolated from the transformants and analyzed by restriction digestion analysis to confirm identity.

A successful transformant is used to inoculate 2 mL of uracil-deficient minimal medium and is grown overnight at 30° C. in an orbital shaker. A 500 µL aliquot of this culture is used to inoculate 50 mL of YEPD medium (Wobbe in Current Protocols in Molecular Biology, Supplement 34:13.0.1-13.13.9 (Wiley, 1996)) (10 g/L yeast extract, 20 g/L peptone, 20 g/L glucose), and the culture is grown at 30° C. in a shaker. In a separate experiment, identical to the above, except that 40 g/L glucose is used, 6-MSA was isolated at a level of >3 grams/liter. In another separate experiment identical to the above, except that 5 g/L glucose was used, 6-MSA was isolated with a >60% conversion from glucose on a molar basis.

Cells are collected by centrifugation of 500 µL aliquots of the culture taken after 24 and, 48 and 72 hours of growth and lysed by boiling in 50 µL of 2×SDS gel loading buffer for about 2 minutes. The cell lysates are analyzed by loading onto 12% SDS-PAGE gels. Bands corresponding to the expected size of 6-MSAS are observed at ca. 190 kD and the OSAS AviM protein, at ca. 145 kD.

6-MSA and OSA are isolated from the yeast supernatants as described previously (Kealey et al., Proc Natl Acad Sci USA 95:505-9, 1998), and identified by comparison with known standards on thin layer chromatography (TLC) plates, and by HPLC.

The purified 6-MSA and OSA are then decarboxylated using known chemical methods to give m-cresol and orcinol or, alternatively are decarboxylated using a recombinant or natural 6-MSA decarboxylase such as the enzyme from *P. patulum*, the 6-MSA decarboxylase PatG from *A. clavatus*, an OSA decarboxylase such as that from *Gliocladium roseum*, or a 2,3-dihydroxybenzoic acid decarboxylase such as that from *A. niger*, or 5-carboxyvanillate decarboxylase from *Sphingomonas paucimobilis* SYK-6. The m-cresol and orcinol products are identified by TLC and HPLC using known standards.

Then, the hydroxyl group of m-cresol is removed by chemical reduction, practicing known methods to yield toluene, e.g. by heating and then distillation with zinc powder. The toluene is further reduced to saturate the aromatic ring to yield methylcyclohexane, a suitable energy source that is saturated and highly desirable for use in jet fuel. Alternatively, m-cresol is reduced and deoxygenated to methylcyclohexane directly, by methods described in patent application WO/2006/086457 using metal catalysts to effect hydrogenation and deoxygenation. m-Cresol is also reduced by standard methods to methylcyclohexanol, which can be used in jet fuel, and can also be used in gasoline.

Example 2

Production of m-Cresol Directly in *S. cerevisiae*

A yeast strain is constructed wherein the *A. nidulans* npgA gene is integrated into the genome of yeast strain BJ2168 (obtained from the ATCC) by standard methods to create strain Rho100-npgA. Plasmids containing expression systems for the ChB1 gene under the selection of Ura3, and for the expression of the *P. patulum* 6-MSA decarboxylase, or the 6-MSA decarboxylase PatG from *A. clavatus*, under selection control through Trp1, are sequentially transformed into Rho100-npgA.

The transformed yeast cells are grown in shake flasks containing YEPD media with 2% glucose for 48 and 72 hours, and the supernatants analyzed for the production of m-cresol. Cells are removed by centrifugation, and m-cresol extracted from the media using ethyl acetate for further analysis, quantitation and distillation to high purity.

In a further series of experiments, the two genes are expressed on the same vector using *S. cerevisiae* IRES sequences separating the two genes, expressed from a single promoter. *S. cerevisiae* IRES sequences were compared with respect to their abilities to produce m-cresol from their respective expression systems.

Example 3

Production of Orcinol Directly in *S. cerevisiae*

Plasmids containing expression systems for the OSAS AviM gene from *Streptomyces viridochromogenes* under the selection of Ura3, and for the expression of the PatG decarboxylase from *Aspergillus* clavatus under selection control through Trp1, are sequentially transformed into Rho100-npgA.

The transformed yeast cells are grown in shake flasks containing YEPD media with 2% glucose for 48 and 72 hours, and the supernatants analyzed for the production of orcinol. Cells are removed by centrifugation, and orcinol extracted from the media using ethyl acetate for further analysis, quantitation and distillation to high purity.

In a further series of experiments, the two genes are expressed on the same vector using *S. cerevisiae* IRES sequences separating the two genes, expressed from a single promoter. IRES sequences are compared with respect to their abilities to produce orcinol from their respective expression systems.

Example 4

Conversion of 6-MSA and OSA to m-Cresol and Orcinol Respectively in *S. cerevisiae* Fermentation Supernatants Yeast cells from EXAMPLES 2 and 3 are grown in a batch fed 1 liter fermentor (New Brunswick), using various feedstocks, such as corn sugar, cellulosic sugars and cane sugar. Media is fed and removed at constant rates in continuous flow mode and the media is fed into solutions containing recombinant decarboxylase proteins. The resulting m-cresol and orcinol products are extracted with ethyl acetate for analysis as above.

In a further series of experiments, supernatants containing m-cresol and orcinol are fed directly into columns containing the appropriate immobilized decarboxylase enzymes on suitable matrices. Again, the m-cresol and orcinol products respectively from the column effluents are extracted with ethyl acetate for analysis of production levels as above.

Example 5

Production of 3-methylanisole and 3,5-dimethoxytoluene in *S. cerevisiae*

A third expression system is incorporated into the expression strains of EXAMPLES 2, 3 and 4. Synthetic genes for the O-methyltransferases from *Rosa chinensis* (Lady Hillingdon and Old Blush varietals) rose petals (Scalliet et al., FEBS Letters 523:113-118 (2002) are constructed and placed under the control of the *S. cerevisiae* ADH-2 promoter or *S. cerevisiae* glycolytic enzyme gene promoters.

Strains containing the full complement of expression systems are grown and harvested as described above, and cell supernatants are analyzed for the production of 3-5 methylanisole (1-methoxy-3-methylbenzene), and 3,5-dimethoxytoluene (1,3-dimethoxy-5-methylbenzene), following extraction with ethyl acetate or diethyl ether.

Example 6

Co-Cultivation of Yeast Cells Producing 6-MSA and Cells Producing a Decarboxylase Enzyme

*S. cerevisiae* cells expressing the bacterial 6-MSAS gene ChlB1 from *Streptomyces antibioticus* as above, and the *A. nidulans* npgA protein are grown as described above for 48 hours. An equal volume of media containing *S. cerevisiae* cells expressing the decarboxylase PatG from *A. clavatus*, also grown for 48 hours is added to the culture, and the co-culture incubated for 24 hours at 30° C. Cells are removed by centrifugation, and m-cresol extracted from the media using ethyl acetate for further analysis, quantitation and distillation to high purity.

Example 7

Decarboxylation of 6-MSA by Heating with Powdered Metal Catalysts

Purified 6-MSA is mixed with catalytic quantities of various metal powders and heated at ambient pressure. m-Cresol is allowed to vaporize and condense into a collection vessel. Analysis of the resulting product shows a percentage purity of >99%.

In a specific example, powdered 6-MSA (20 grams) was mixed with zinc powder (2.5 grams) and heated in a retort until all the solids liquefied. Heating was continued and m-cresol was allowed to vaporize and condense into an ice-cooled flask, giving a yield of 11.35 grams of >99.9% pure colorless m-cresol.

What is claimed is:

1. A modified recombinant host cell for producing a phenolic compound, comprising
   i) a first expression system that comprises at least one nucleotide sequence that encodes a 6-methylsalicylic acid synthase (6-MSAS) or an orsellinic acid synthase (OSAS), capable of being expressed, and
   ii) a second expression system that comprises at least one nucleotide sequence that encodes a holo acyl carrier protein (ACP) synthase, wherein the ACP synthase pantetheinylates said 6-MSAS or OSAS, and
   iii) a third expression system that comprises at least one nucleotide sequence that encodes a functional decarboxylase which catalyzes decarboxylation to form said phenolic compound, such that the product isolated from said cell is a phenolic compound, wherein either:
   the first expression system for 6-MSAS or OSAS and the second expression system for ACP synthase are present on a single vector or on separate vectors, and wherein the third expression system for a functional decarboxylase is present on the same vector as the 6-MSAS or OSAS, or the holo ACP synthase, or both, or is present on a separate vector, or;
   wherein the first, second or third expression systems are integrated into the host cell chromosome or expressed from yeast artificial chromosomes (YACs).

2. The modified cell of claim 1, wherein the phenolic compound is meta-cresol or orcinol.

3. The modified cell of claim 1 wherein said 6-MSAS is from a fungus or a prokaryote.

4. The modified cell of any one of claims 1, 2, and 3, wherein the nucleotide sequence encoding the decarboxylase is selected from the group consisting of the 6-MSA decarboxylase gene from *P. patulum*, the PatG gene from *Aspergillus clavatus*, the OSA decarboxylase gene from *Gliocladium roseum*, the 2,3-dihydroxybenzoic acid decarboxylase genes from *Aspergillus* species, and the 5-carboxyvanillate decarboxylase gene from *Sphingomonas paucimobilis* SYK-6.

5. The modified cell of claim 1 wherein said 6-MSAS or OSAS and said holo ACP synthase are expressed from a dicistronic messenger RNA.

6. The modified cell of claim 1 wherein the host organism is selected from the group consisting of *Saccharomyces cerevisiae*, *Pichia pastoris*, and an *Aspergillus* species.

7. A method of producing a phenolic compound, the method comprising
   a) providing a modified recombinant host cell comprising
      i) a first expression system that comprises at least one nucleotide sequence encoding a 6-methylsalicylic acid synthase (6-MSAS) or an orsellinic acid synthase (OSAS), capable of being expressed;
      ii) a second expression system that comprises at least one nucleotide sequence encoding a holo acyl carrier protein (ACP) synthase, wherein the ACP synthase pantetheinylates said 6-MSAS or OSAS; and
      iii) a third expression system that comprises at least one nucleotide sequence that encodes a functional decarboxylase;
   b) producing a first phenolic compound in the recombinant host cell; and
   c) synthesizing a second phenolic compound from the first phenolic compound, wherein recombinant decarboxylase catalyzes decarboxylation of the first phenolic compound to form the second phenolic compound, wherein either:
   the first expression system for 6-MSAS or OSAS and the second expression system for ACP synthase are present on a single vector or on separate vectors, and wherein the third expression system for a functional decarboxylase is present on the same vector as the 6-MSAS or OSAS, or the holo ACP synthase, or both, or is present on a separate vector, or;
   wherein the first, second or third expression systems are integrated into the host cell chromosome or expressed from yeast artificial chromosomes (YACs).

8. The method of claim 7, wherein the first phenolic compound is 6-MSA or orsellinic acid (OSA) and wherein the second phenolic compound is meta-cresol or orcinol.

9. The modified cell of claim 1, wherein the phenolic compound is an alkylated phenolic compound and wherein the modified host cell further comprises
   (iv) a fourth expression system that comprises at least one nucleotide sequence that encodes an O-methyltransferase (OMT), such that the product isolated from said cell is an alkylated phenolic compound.

10. The modified cell of claim 9, wherein the alkylated phenolic compound is 3-methylanisole or 3,5-dimethoxytoluene.

11. The modified cell of claim 9, wherein the OMT is encoded by a *R. chinensis* gene selected from the group consisting of OOMT1, OOMT2, OOMT3, OOMT4, COMT1.

12. The method of claim 7, which is for producing an alkylated phenolic compound, the method comprising d) isolating the second phenolic compound produced in the recombinant host cell; and e) alkylating the second phenolic compound of step d) to form the alkylated phenolic compound by treating with an alkylating agent.

13. The method of claim 12, wherein the second phenolic compound is meta-cresol or orcinol.

14. The method of any one of claims 7, 8, 12, and 13, wherein the nucleotide sequence encoding the decarboxylase is selected from the group consisting of the 6-MSA decarboxylase gene from *P. patulum*, the PatG gene from *Aspergillus clavatus*, the OSA decarboxylase gene from *Gliocladium roseum*, the 2,3-dihydroxybenzoic acid decarboxylase genes from *Aspergillus* species, and the 5-carboxyvanillate decarboxylase from *Sphingomonas paucimobilis* SYK-6.

* * * * *